US012409448B2

(12) United States Patent
Derfus et al.

(10) Patent No.: US 12,409,448 B2
(45) Date of Patent: Sep. 9, 2025

(54) SAMPLE PREPARATION DEVICE AND METHODS FOR USING SAME

(71) Applicant: Abbott Diagnostics Scarborough, Inc., Scarborough, ME (US)

(72) Inventors: Austin M. Derfus, Solano Beach, CA (US); Karthikeyan Kumaravadivelu, San Diego, CA (US); Neil Quitoviera, Temecula, CA (US); Adrian P. Crute, San Diego, CA (US); Timothy L Higby, Temecula, CA (US); Richard B. Roth, San Diego, CA (US); Aric Joneja, San Diego, CA (US); Torsten Gliewe, San Diego, CA (US)

(73) Assignee: Abbott Diagnostics Scarborough, Inc., Scarborough, ME (US)

( * ) Notice: Subject to any disclaimer, the term of this patent is extended or adjusted under 35 U.S.C. 154(b) by 697 days.

(21) Appl. No.: 17/789,762

(22) PCT Filed: Dec. 23, 2020

(86) PCT No.: PCT/US2020/066926
§ 371 (c)(1),
(2) Date: Jun. 28, 2022

(87) PCT Pub. No.: WO2021/138210
PCT Pub. Date: Jul. 8, 2021

(65) Prior Publication Data
US 2023/0039793 A1    Feb. 9, 2023

Related U.S. Application Data

(60) Provisional application No. 63/066,683, filed on Aug. 17, 2020, provisional application No. 63/050,251, (Continued)

(51) Int. Cl.
*B01L 3/00* (2006.01)
*C12N 15/10* (2006.01)

(52) U.S. Cl.
CPC .......... *B01L 3/502* (2013.01); *C12N 15/1013* (2013.01); *B01L 2200/0647* (2013.01);
(Continued)

(58) Field of Classification Search
CPC ............. B01L 3/502; B01L 2200/0647; B01L 2300/042; B01L 2300/0832;
(Continued)

(56) References Cited

U.S. PATENT DOCUMENTS 6,374,684 B1 *   4/2002   Dority .................... B01L 3/502
                                                          73/864.81
10,378,045 B2    8/2019   Connolly et al.
(Continued)

*Primary Examiner* — Samuel P Siefke
(74) *Attorney, Agent, or Firm* — Edward J. Baba; Mandar A. Joshi; Bozicevic, Field & Francis LLP

(57) ABSTRACT

Aspects of the present disclosure include sample preparation cartridges including a cylindrical structure and one or more covers. The cylindrical structure further includes a top, a bottom, an annular wall, a plurality of cavities in the annular wall that form a plurality of open-sided chambers on the annular wall and one or more interconnections providing fluidic communication between the plurality of chambers. The one or more covers cover the open side of the plurality of chambers. Also provided is a cylinder housing comprising one or more magnets. The sample preparation cartridge is removably disposed into the cylinder housing or adjacent to the cylinder housing. Methods of using the sample preparation device are also provided.

44 Claims, 22 Drawing Sheets

Related U.S. Application Data filed on Jul. 10, 2020, provisional application No. 63/023,659, filed on May 12, 2020, provisional application No. 62/955,259, filed on Dec. 30, 2019.

(52) U.S. Cl.
CPC . *B01L 2300/042* (2013.01); *B01L 2300/0832* (2013.01); *B01L 2400/043* (2013.01)

(58) Field of Classification Search
CPC ....... B01L 2400/043; B01L 2300/0858; B01L 2400/0478; B01L 3/502761; B01L 2200/0668; C12N 15/1013
See application file for complete search history.

(56) References Cited

U.S. PATENT DOCUMENTS

| | | |
|---|---|---|
| 2008/0131949 A1 | 6/2008 | Bortolin et al. |
| 2011/0152720 A1 | 6/2011 | Zappia et al. |
| 2014/0127790 A1 | 5/2014 | Malik et al. |
| 2018/0087097 A1* | 3/2018 | Toumazou .......... B01L 3/50273 |
| 2019/0046972 A1 | 2/2019 | Mulakkapurath Narayanan et al. |
| 2019/0270086 A1 | 9/2019 | Harding et al. |
| 2019/0293673 A1* | 9/2019 | Wescott ............... G01N 1/4077 |
| 2019/0338346 A1 | 11/2019 | Connolly et al. |

* cited by examiner

FIG. 2
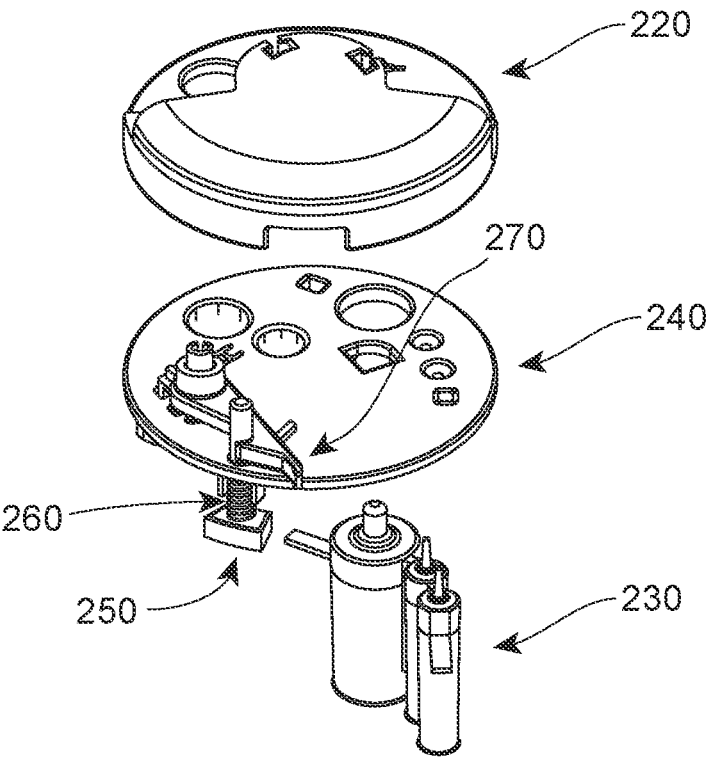
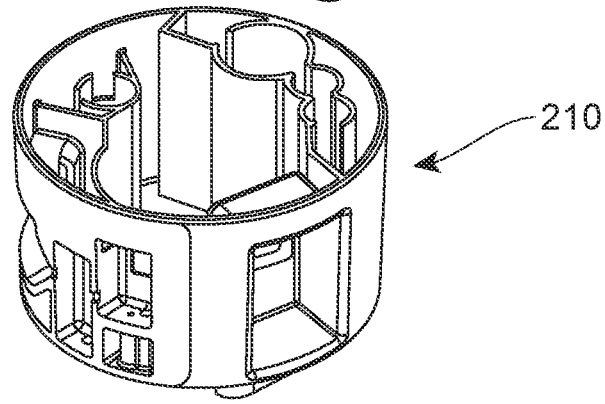
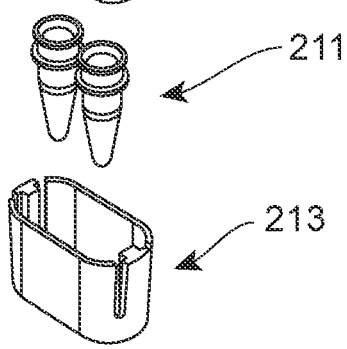

700

FIG. 14
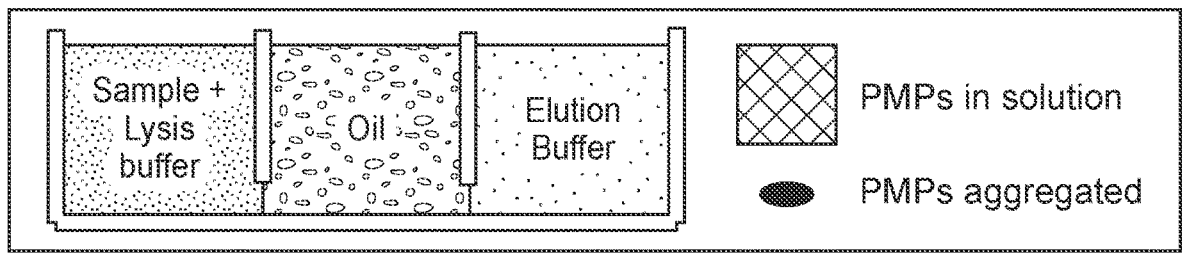
1) Lyse, 2) Bind
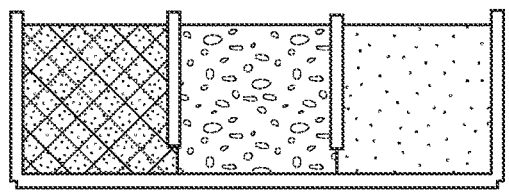
Sample mixed with lysis buffer
3) Wash
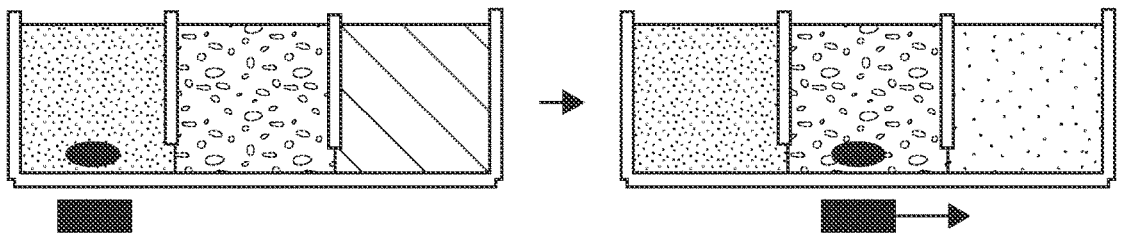
External magnet aggregates PMPs and moves them through the phases
4) Elute
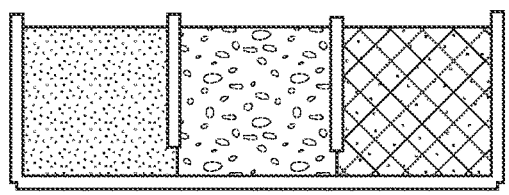
PMPs mixed with elution buffer to release nucleic acid

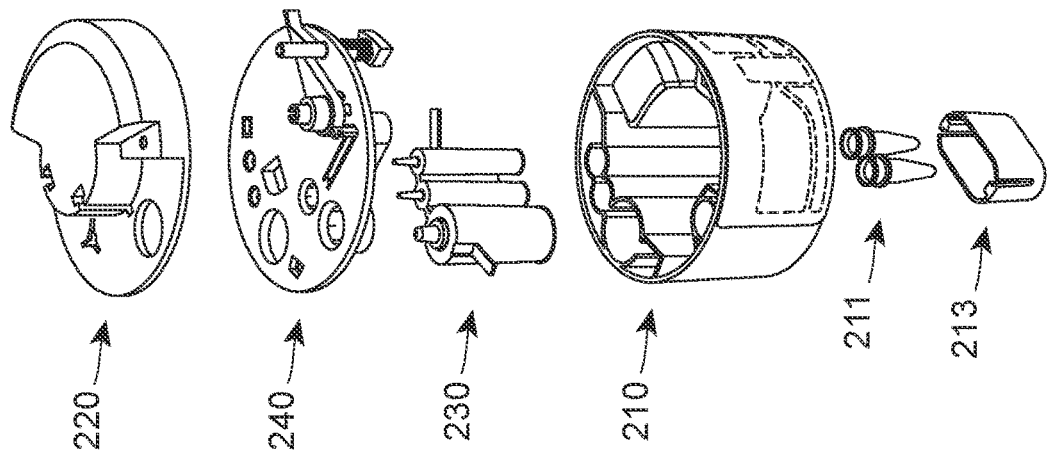
FIG. 17
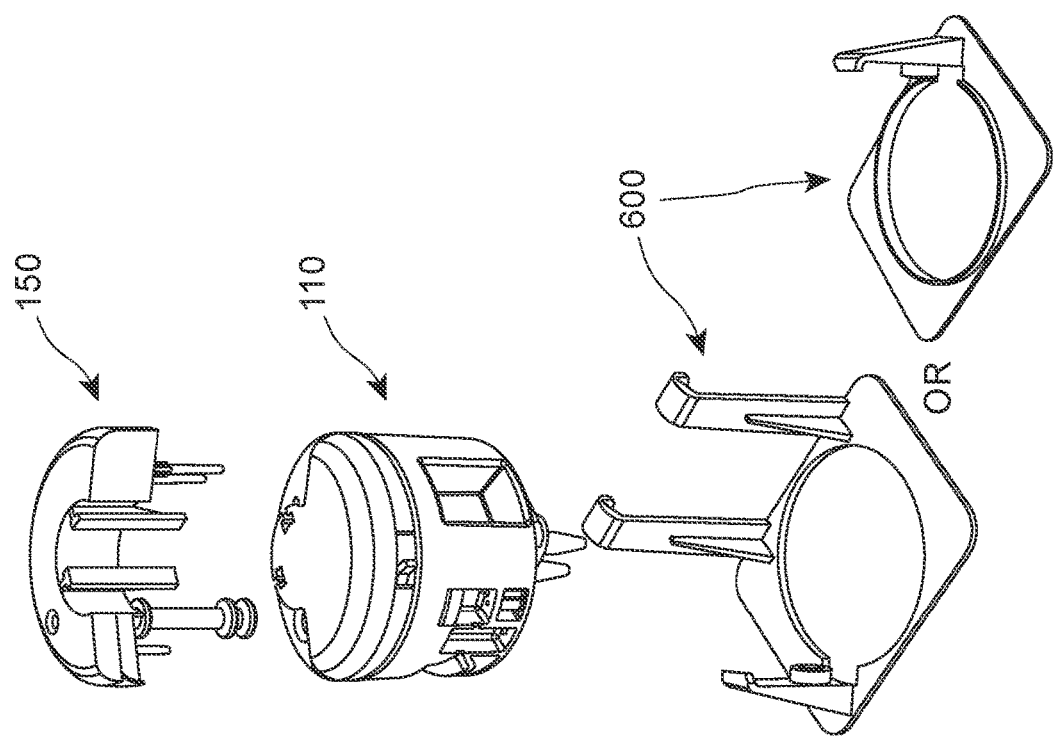

SAMPLE PREPARATION DEVICE AND METHODS FOR USING SAME

CROSS-REFERENCE TO RELATED APPLICATIONS

This application claims the benefit of U.S. Provisional Patent Application No. 62/955,259, filed Dec. 30, 2019, U.S. Provisional Patent Application No. 63/023,659, filed May 12, 2020, U.S. Provisional Patent Application No. 63/050, 251, filed Jul. 10, 2020, and U.S. Provisional Patent Application No. 63/066,683, filed Aug. 17, 2020, which applications are incorporated herein by reference in their entirety.

INTRODUCTION

Nucleic acid isolation and purification is a set of molecular biology techniques used for the extraction of DNA and RNA for use in downstream applications. Nucleic acid isolation and purification approaches include column-based isolation and purification, reagent-based isolation and purification, magnetic bead-based isolation and purification, and other technologies. Reagents, kits and instruments that find use in isolating and purifying nucleic acids are available. Poor sample preparation can lead to suboptimal results in downstream applications, and it is for this reason that optimized versions of kits have emerged to address variation in sample source, be it blood, plant tissue, fungi, or bacteria.

A sample preparation process includes releasing a nucleic acid target from its native biological source (e.g., lysis of cells, such as patient cells or lysis of microorganisms, such as, virus, bacteria, fungi, etc.) using chaotropic nucleic acid extraction technology, binding of nucleic acids to a solid phase (e.g., paramagnetic particles) using silica or iron oxide nucleic acid chemistry, separation of the solid phase from the residual lysis solution using magnetic separation technology, washing to remove unwanted materials, and elution or separation of nucleic acid from the solid phase using fluid handling technology. At the completion of the sample preparation protocol, the sample is transferred to a PCR component of a device for nucleic acid detection.

SUMMARY

Aspects of the present disclosure include sample preparation cartridges, sample preparation systems and sample preparation devices for preparing a sample for e.g., enriching or isolating a target analyte such as nucleic acid present in the sample.

The sample preparation cartridge includes a cylindrical structure with plurality of chambers disposed along the annular wall of the structure, the annular wall comprising cavities forming an open side of each of the chambers and a cover affixed over the exterior surface of the annular wall to cover and fluidically seal the open side of the chambers.

The sample preparation system includes the sample preparation cartridge and a cylinder housing comprising one or more magnets. The cartridge is removably disposed into the cylinder housing. In some embodiments, the magnet is external to the cartridge and is used to transfer paramagnetic particles between chambers of the cartridge.

The sample preparation device includes a cavity for reversibly engaging a portion of the cartridge. The sample preparation device may include a magnet disposed therein and configured for transferring paramagnetic particles between chambers of the cartridge. The sample preparation device may include a cavity for reversibly engaging a portion of the cartridge and a surface for attaching the cylinder housing. Certain embodiments also provide sample preparation devices that actuate rotation of a cartridge disposed therein using a motor. The motor can be automated. The motor can also be controlled by a computer program, which when executed by a processor, causes the motor to perform rotate the cartridge in a predetermined manner.

Methods of using the sample preparation device are also provided. The methods may be semi-automated or completely automated to perform the sample preparation.

BRIEF DESCRIPTION OF THE FIGURES

FIG. 2 shows certain components of a sample preparation cartridge according to one embodiment of the present disclosure in an exploded view. In this view, the cylindrical structure, the buffer pack, the sealing plate and the protective cover are broken out for illustration.

FIG. 14 shows a schematic representation of the materials and steps involved in sample preparation.

FIG. 17 shows various components of an example of a sample preparation cartridge (integrated sample processing device (ISPD)) and cylinder housing designed to isolate nucleic acids using paramagnetic particles.

DETAILED DESCRIPTION

Figure 1A:
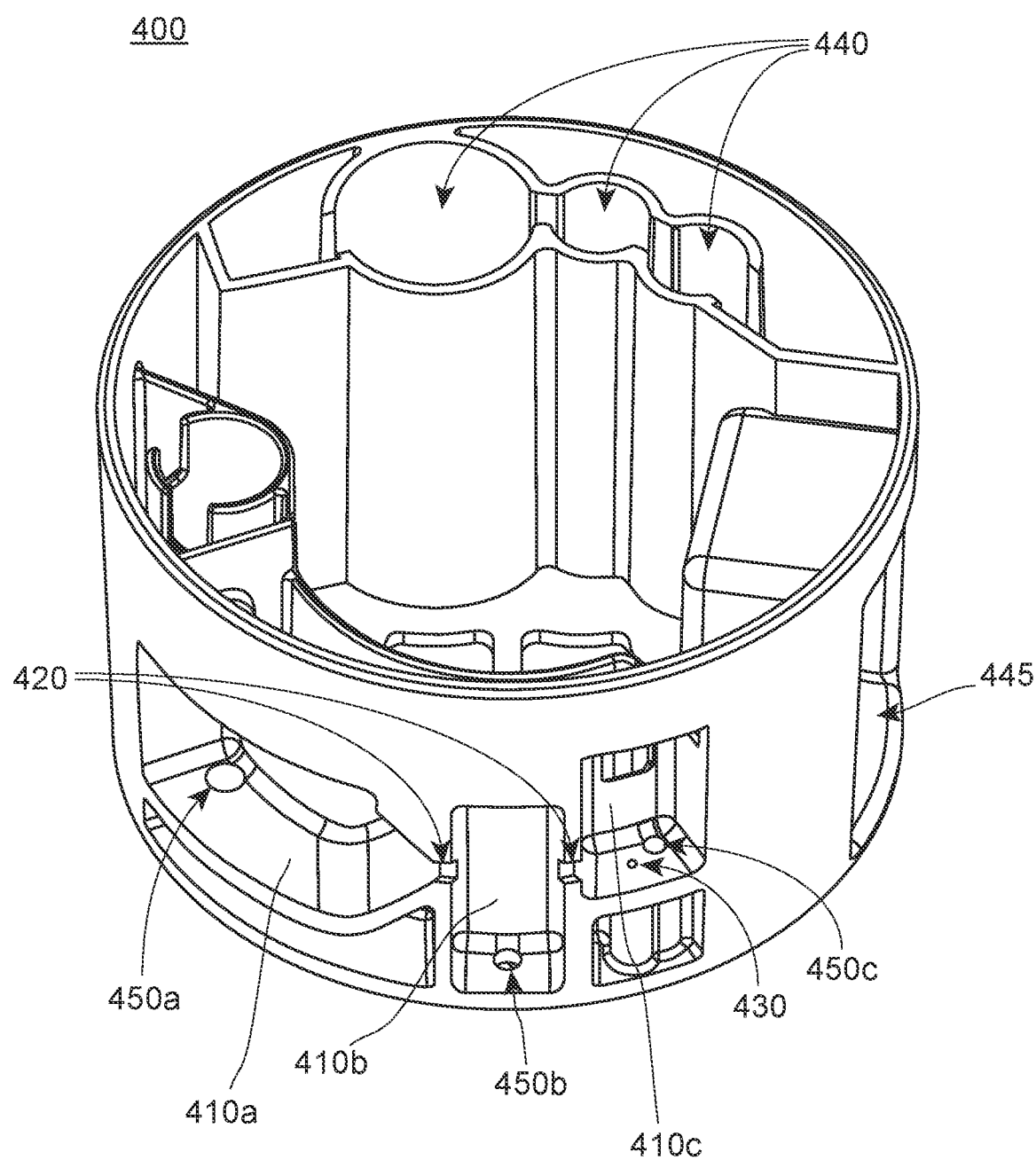
FIG. 1A shows a sample preparation cartridge according to one embodiment. Open sides of the chambers 410a, 410, and 410c are visible.

Aspects of the present disclosure include sample preparation cartridges, sample preparation systems and sample preparation devices for preparing a sample for e.g., enriching or isolating a target analyte such as nucleic acid present in the sample.

The sample preparation cartridge includes a cylindrical structure with plurality of chambers disposed along the annular wall of the structure, the annular wall comprising cavities forming an open side of each of the chambers and a cover affixed over exterior surface of the annular wall to cover and fluidically seal the open side of the chambers.

The sample preparation system includes the sample preparation cartridge and a cylinder housing comprising one or more magnets. The cartridge is removably disposed into the cylinder housing. In some embodiments, the magnet is external to the cartridge and is used to transfer the magnetic particles between chambers of the cartridge.

The sample preparation device includes a cavity for reversibly engaging a portion of the cartridge. The sample preparation device may include a magnet disposed therein and configured for transferring the magnetic particles between chambers of the cartridge. The sample preparation device may include a cavity for reversibly engaging a portion of the cartridge and a surface for attaching the cylinder housing. Certain embodiments also provide sample preparation devices that actuate rotation of a cartridge disposed therein using a motor. The motor can be automated. The motor can also be controlled by a computer program, which when executed by a processor, causes the motor to perform rotate the cartridge in a predetermined manner.

Methods of using the sample preparation device are also provided. The methods may be semi-automated or completely automated to perform the sample preparation.

Before the present sample preparation device and methods are described in greater detail, it is to be understood that the present disclosure is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the present sample preparation cartridges, methods, and sample preparation units. The upper and lower limits of these smaller ranges may independently be included in the smaller ranges and are also encompassed within the sample preparation cartridges, methods, and sample preparation units, subject to any specifically excluded limit in the stated range. Where the stated range includes one or both of the limits, ranges excluding either or both of those included limits are also included in the sample preparation cartridges, methods, and sample preparation units.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present sample preparation cartridges, methods, and sample preparation units, representative illustrative sample preparation cartridges, methods, and sample preparation units are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present sample preparation cartridges, methods, and sample preparation units. Any recited method can be carried out in the order of events recited or in any other order which is logically possible.

Sample Preparation Cartridges

As summarized above, aspects of the present disclosure include sample preparation cartridges. According to certain embodiments, the sample preparation cartridges have a substantially cylindrical shape. The sample preparation cartridges include a cylindrical structure including a top end, a bottom end and an annular wall extending between the top and bottom ends. The cylindrical structure includes a plurality of chambers located in the annular wall, where the chambers extend between an exterior surface of the annular wall and an interior of the cylindrical structure, where the annular wall comprises cavities forming an open side of each of the chambers; and one or more channels providing fluidic communication between the plurality of chambers, where the channels are formed by recesses in the annular wall and comprise an open side; and one or more covers affixed over exterior surface of the annular wall to cover and fluidically seal the open side of the chambers and the open side of the recesses.

Additionally, in certain embodiments, the sample preparation cartridge may also include: a buffer pack, a sealing lid assembly, a protective cover, and a cap. The cartridge may also include a sample input component. The sample preparation cartridge is configured for use with a cylinder housing comprising a magnet.

Each of these components is described in greater detail below.

Cylindrical Structure

By cylindrical, it is meant that the cylindrical structure may be substantially a right circular cylinder. The cylindrical structure may be rotatable around the axis formed by a line connecting the center of the bottom end of the cylindrical structure with the center of the top end of the cylindrical structure. For example, the cylindrical structure may rotate clockwise when the cylindrical structure is viewed from above looking down onto the top of the cylindrical structure or may rotate counterclockwise. Alternatively, the cylindrical structure may rotate both clockwise and counterclockwise. In some instances, the range of motion of the cylindrical structure may encompass an entire revolution or less around the axis of the cylinder, such as three-fourths of a revolution, or one-half of a revolution or one-third of a revolution. In certain embodiments, the cylindrical structure may rotate a full revolution in the clockwise direction and a full revolution in the counterclockwise direction. In certain embodiments, the cylindrical structure may rotate a full revolution in the clockwise direction and less than a full revolution in the counterclockwise direction, or vice versa. Rotation of the cylindrical structure may be used for mixing contents of the one or more chambers or positioning a magnet present in the cylinder housing adjacent a chamber to cause aggregation of magnetic particles present in the chamber and/or to transfer aggregated magnetic beads from one chamber to another, etc.

As summarized above, the cylindrical structure comprises a plurality of cavities in the annular wall that form a plurality of open-sided chambers on the annular wall. For example, the plurality of cavities may be indentations in the annular wall that deform the continuous surface of the annular wall. By open sided, it is meant that the annular wall does not cover such side of the chamber. In certain instances, the deformed annular wall may form closed sides of the chambers, and the area corresponding to the side of the annular wall that was deformed to form the cavity may form the open side of the chambers.

According to certain embodiments, the open sides of the plurality of chambers are located on the exterior of the annular wall. For example, the annular wall may be deformed inward from the outside to form an inwardly deformed cavity in the annular wall. In such case, the open side of the chamber may be the area corresponding to the side of the annular wall that was deformed inward to form the cavity. In such instances, the annular wall that has been inwardly deformed may form closed sides of the chambers. The volume of a chamber may represent a measurement corresponding to the volume of the indentation in the annular wall. The chambers may be any convenient volume, and in some instances may vary from 1 cm$^3$ to about 5 cm$^3$, such as 1 cm$^3$ to 3 cm$^3$ or 2 cm$^3$ to 5 cm$^3$. In other instances, the chambers can contain any convenient volume of fluid, and in some instances may vary from 1 µL to about 5,000 µL, such as 1 µL to 100 µL or 1,000 µL to 3,000 µL or 2,000 µL to 5,000 µL. Each chamber of the plurality of chambers may have the same volume or may have different volumes. The depth of the chamber, measured as the distance from the outside surface of the annular wall to the inner side of the chamber, may be any convenient size, and in some instances, may be 0.1 cm or greater, such as 1 cm or 5 cm. Each chamber of the plurality of chambers may have the same depth or may have different depths.

According to certain embodiments, the plurality of chambers is positioned proximal to each other on the annular wall. For example, the distance between a lateral border of a first chamber and the closest lateral border of a second chamber may be about 0.1 cm or more, such as 0.5 cm to 1 cm, e.g., 0.5 cm or 0.75 cm or 5 cm. The distances between lateral sides of pairs of chambers positioned next to each other may be the same for the plurality of chambers or may differ.

As summarized above, sample preparation cartridges include one or more channels that provide fluidic communication between the plurality of chambers. In certain aspects, the channels are wide enough that one or more PMPs, e.g., aggregates of PMPs can be transported therethrough. In certain embodiments, one or more of the channels between chambers are formed by recesses in the annular wall. By recess in the annular wall, it is meant an indentation or a cavity in the annular wall capable of providing fluidic communication between chambers. In some cases, the recess is formed in the outside surface of the annular wall, such that a first chamber and a second chamber that are formed with open sides on the exterior surface of the annular wall are interconnected by a recess in the outside surface of the annular wall between such first chamber and second chamber. The recesses in the annular wall may be any convenient length, width and depth.

In certain embodiments, the recesses are positioned on the lateral sides of the plurality of chambers. By lateral sides of the plurality of chambers, it is meant the left- or right-hand sides and not the top or the bottom sides of the chambers, when the axis of the cylindrical structure formed between the center of the bottom end and the center of the top end of the cylindrical structure is oriented vertically. By positioning recesses on the lateral sides of the plurality of chambers, it is meant that a recess may interconnect the right-hand side of a first chamber with the left-hand side of a second chamber, such that such first and second chambers are in fluidic communication with each other via the recess. Recesses between chambers may be substantially straight lines between a point on a first chamber and a point on a second chamber. A recess between a first and second chamber may have substantially the same width and depth in the annular wall across the entire length of the recess or may vary. Recesses between different pairs of chambers may have different dimensions or same dimensions. Recesses may be shaped as convenient such that PMPs may be translated therethrough.

In certain embodiments, the recesses are positioned on the lateral sides of one or more chambers at a substantially constant height above the bottom end of the cylindrical structure. In these embodiments, the recesses between pairs of chambers may be substantially linear. In these embodiments, the recesses and the chambers may be shaped such that a path exists starting from the leftmost position on the leftmost chamber through each of the plurality of chambers to the rightmost position of the rightmost chamber, in a straight line. The straight line is generally substantially parallel to the bottom end of the cylindrical structure. The recesses on the lateral sides of one or more chambers may be positioned at any convenient height above the bottom end of the cylindrical structure. In certain of these embodiments, the height above the bottom end of the cylindrical structure at which the recesses are positioned corresponds to the vertical midpoint of one or more of the chambers.

The shape of one or more of the plurality of chambers may be substantially in shape of a cube, a cuboid, an ovoid, or a sphere, a combination thereof, or may have an irregular shape. By irregular shape, it is meant that there is no axis of symmetry. By combination of shapes, it is meant that one side of the one or more chambers may be one shape, e.g., a rectangular side while the remainder of the chamber may have another shape, e.g., an oval shape or a spherical shape. Another example of a chamber having a combination of shapes includes a cube or a cuboid with curved corners or an oval or a sphere is certain substantially flat walls. In certain examples, the side of the one or more chambers formed by the cover and the outer surface of the cylindrical structure may be shaped as a square or rectangle, optionally with curved corners and the remainder of the one or more chambers may have an ovoid shape. In another embodiment, the chambers may have an ovoid shape. In some instances, the chamber is positioned such that the an axis of symmetry along the shortest part of the ovoid is parallel to the bottom of the cylindrical structure. In other embodiments, the shape of one or more of the plurality of chambers is generally rectangular. By generally rectangular chamber, it is meant that the two-dimensional shape of the indentation into the annular wall is longer than it is wider. The height and width of each chamber may be any convenient height and width. The height and width of each rectangular chamber may be identical or may differ.

In certain embodiments, the shape of a chamber connected to another chamber by one or more channels is such that with respect to a lateral portion of the chamber that is proximal to a channel, the height of the chamber at each lateral position of the chamber decreases the closer such position is to the channel. In some cases, the height of such chamber at each lateral position decreases linearly so as to form a tapered region. Such a tapered entrance to the recess may facilitate transport of aggregated PMPs from the chambers to the channel.

In certain embodiments, one or more of the chambers comprises a drain hole. By drain hole, it is meant a hole through which fluid may exit the chamber. For example, fluid may drain from a drain hole located at the bottom of a chamber under the influence of the force of gravity. Alternatively, fluid may be plunged out of the chamber upon the application of pressure to fluid in the chamber by a plunger. In certain instances, only one of the chambers configured for use as an elution chamber, by filling with an elution buffer, may include a drain hole while the remainder of the chambers, e.g., the first and second chambers may not include a drain hole.

The one or more of the chambers may include an opening which is configured for venting of the chamber and/or filling of the chamber with a fluid. In certain instances, the opening may also be used for draining of fluid from the chamber.

In certain embodiments, the interior of the cylindrical structure comprises one or more wells. By wells, it is meant one or more enclosures within the inside of the cylindrical structure. The enclosures may be any convenient size or shape. For example, the enclosures may be substantially cylindrical, with a closed bottom end, an annular wall, and an open top end. In these embodiments, cylindrical structures may further comprise channels in the cylindrical structure that provide fluidic communication between such wells and one or more of the plurality of chambers. In some instances, each well is interconnected with a distinct chamber via one or more channels.

In certain embodiments, the plurality of chambers forms a first chamber, a second chamber and a third chamber. In certain embodiments, the first chamber is adjacent to the second chamber; the second chamber is adjacent to the first and third chambers; and the third chamber is adjacent to the second chamber. In certain embodiments, the cylindrical structure further includes a first recess in the annular wall providing fluidic communication between the first and second chambers, and a second recess in the annular wall providing fluidic communication between the second and third chambers. In certain embodiments, the first chamber is a lysis chamber; the second chamber is an immiscible phase chamber; and the third chamber is an elution chamber. By lysis chamber, it is meant a chamber that during use of the sample preparation cartridge contains lysis buffer, such as a fluid that is a lysis buffer. By immiscible phase chamber, it is meant a chamber that during use of the sample preparation cartridge contains an immiscible phase, such as a fluid that is immiscible with aqueous phase. In some cases, the immiscible phase is oil. In other cases, the immiscible phase is air. By elution chamber, it is meant a chamber that during use of the sample preparation device contains an elution buffer, such as a fluid that is an elution buffer.

The first chamber may include an opening at the top of the chamber. This opening may be configured as an inlet. The inlet may be configured for introducing a lysis buffer, a sample, and/or a mixture thereof. Thus, the inlet may have a diameter compatible for pipetting, injecting, or pumping a lysis buffer, a sample, and/or a mixture thereof. In some cases, the second chamber may also include an opening at the top of the chamber. This opening may be configured as an inlet for introducing an immiscible phase, e.g., oil into the second chamber. In some cases, the third chamber may also include an opening at the top of the chamber. This opening may be configured as an inlet for introducing an elution buffer into the third chamber.

In certain examples, the first chamber may include a compartment positioned on the bottom region or underneath the bottom region of the first chamber. The compartment may include an opening fluidically connecting the compartment to the interior of the first chamber. The compartment may include paramagnetic particles (PMPs). The PMPs may be lyophilized. In certain embodiments, the first chamber includes an opening at the bottom of the chamber, wherein the opening is configured as an inlet for lysis buffer and wherein the first chamber comprises an opening at the top of the first chamber configured as a sample inlet. In certain embodiments, the compartment includes an inlet fluidically connecting the compartment to a channel and an outlet fluidically connecting the compartment to the interior of the first chamber.

Paramagnetic particles (PMPs) and magnetic particles are used herein interchangeably and refer to particles that are magnetically responsive. Magnetically responsive particles include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP. PMPs may be comprised of a paramagnetic material enclosed in a non-magnetic polymer, such as, magnetic materials covered with a polymeric material or magnetic material embedded in a polymer matrix. Such particles may be referred to as magnetic or paramagnetic beads.

In certain examples, the second chamber may not include an opening other than the interconnections with the first and third chambers. The second chamber may contain air. When the first and third chambers are filled with a liquid the air in the second chamber is compressed due to lack of a vent in the second chamber. The compressed air serves as a "wash" environment for PMPs transferred from the first chamber to the third chamber via the second chamber comprising the compressed air.

In certain examples, the third chamber includes an opening at a bottom region of the chamber. The opening is configured for draining the third chamber. The third chamber may include an opening at a bottom region of the chamber wherein the opening is distinct from the opening for draining the third chamber and is configured for filling the third chamber. In certain cases, the draining hole may have a smaller diameter than the filling hole such that the draining hole does not allow liquid to pass through under atmospheric pressure and requires a higher pressure to allow passage of liquid. In some cases, the opening at the bottom of the third chamber is fluidically connected to one or more collection containers. The collection containers may be two separate tubes, e.g., thin wall polypropylene tube suitable for PCR. The opening at the bottom of the third chamber may be fluidically connected to two channels that split from the opening to fill the two collection containers with substantially equal volume of liquid drained from the third chamber.

A cylindrical structure according to one embodiment is shown in FIG. 1A. In this example, the cylindrical structure 400 includes three cavities in the annular wall that form three open-sided chambers 410a, 410b, and 410c on the annular wall and two recesses that form open-sided interconnections 420. As seen, the open sides of the chambers 410a, 410b, and 410c are located on the exterior of the annular wall, and the chambers 410a, 410b, and 410c are positioned adjacent to each other. The two interconnections 420 between the chambers 410a, 410b, and 410c provide fluidic communication between the chambers. In this example, the interconnections 420 are channels that are recesses in the annular wall, and the interconnections 420 are positioned on the lateral sides of the plurality of chambers 410a, 410b, and 410c. As illustrated in the figure, the recesses that form interconnections 420 between the chambers 410a, 410b, and 410c are at a substantially constant height above the bottom end of the cylindrical structure 400. Also seen in the example, is a drain hole 430 in one of the chambers. Each chamber additionally includes a vent (450a, 450b, and 450c). The vent can be used to vent air from the chambers. Alternatively, or in addition, the vents may also be used as an inlet for filling the chambers with a liquid. In certain embodiments, the second chamber 410b may be an air chamber and does not include the vent 450b. In addition, the cylindrical structure 400 includes wells 440. As seen, the wells 440 are positioned in the interior of the cylindrical structure 400.

Covers

As summarized above, sample preparation cartridges include one or more covers that cover the open sides of the plurality of chambers and the interconnections to form channels. In certain aspects, a cover curves to mate with the outside surface of the cylindrical structure. By curves, it is meant that the cover is substantially not flat when attached to the cylindrical structure. By cover the open side of the plurality of chambers, it is meant that the cover may be positioned so that it lies over the open side of a chamber formed on the annular wall. In certain instances, when the cover covers a chamber, the chamber is not accessible from the outside of the cylindrical structure. When the cover covers a chamber, a fluid disposed in the chamber is contained in the chamber. Use of a cover to form a wall of the chambers in the cylindrical device allows for a wall that is significantly less thick that the annular wall of the cylindrical structure. Use of a cover to form a wall of the chambers in the cylindrical device allows for a wall that is made from a material different from the material of the cylindrical structure. In certain embodiments, a single cover may cover all of the plurality of chambers or may cover a subset of the plurality of chambers and all or a subset of the interconnections between the chambers. A cover may be any convenient size and shape, and the size and shape of the cover may vary.

A cover may be made from any suitable material that can be curved and attached to the exterior surface of the annular wall. For example, the cover may be made from plastic, metal, paper, glass, and the like. If metal material is used for the cover, the metal may be non-magnetic, i.e., not include substantial amount of iron. A paper cover may include a non-wettable coating, e.g., a wax coating. The cover may be substantially opaque or substantially transparent. The cover may be attached to the annular wall by any suitable means such as via an adhesive, locally heating the exterior of the annular wall or the cover or both, by snapping the cover into a groove(s) created in the annular wall, by screwing the cover into the annular wall, and the like. The cover may be sufficiently thin so as to not significantly decrease in the chambers the magnetic force of an external magnet. For example, the cover may be sufficiently thin to allow paramagnetic particles (PMPs) present in a chamber to be aggregated in response to the external magnet being located adjacent the chamber and to allow the aggregated PMPs to traverse thorough a channel connecting adjacent chambers in response to relative movement of the cylindrical structure and the external magnet. The cover may have a thickness of less than 1 cm, less than 0.5 cm, less than 0.1 cm, e.g., 1 mm-5 mm. In certain embodiments, the cover may be a film, e.g., an adhesive film.

According to certain embodiments, the cover fluidically seals the open sides of the plurality of chambers. By fluidically seals the open sides of the plurality of chambers, it is meant that when the cover is positioned on the cylindrical structure, the space inside the chambers is not in fluidic communication with the space outside the cylindrical structure, via the open side of the chambers.

According to certain embodiments, the interior surface of the cover facilitates movement of PMPs thereon. The PMPs used in sample preparation are capable of having an analyte of interest attached thereon, e.g., capable of having nucleic acids attached thereon. Nucleic acids may be attached to surface of PMPs by silica or iron oxide nucleic acid chemistry. By facilitating movement of PMPs, it is meant that the interior surface of the cover may be configured such that PMPs may be more reliably translated from a first position on the cover to a second position on the cover while remaining in contact with the interior surface of the cover. For example, the interior surface of the cover may be polished to reduce friction between PMPs and the interior surface of the cover as the PMPs move along the cover. By translated from a first position on the cover to a second position on the cover, in certain cases, it is meant that the PMPs are moved along the interior of the cover; or, in certain cases, it is meant that the PMPs are held in a fixed position while the interior of the cover is moved from a first position to a second position; or, in certain cases, it is meant that both the PMPs are moved and the cover is moved.

Figure 1B:
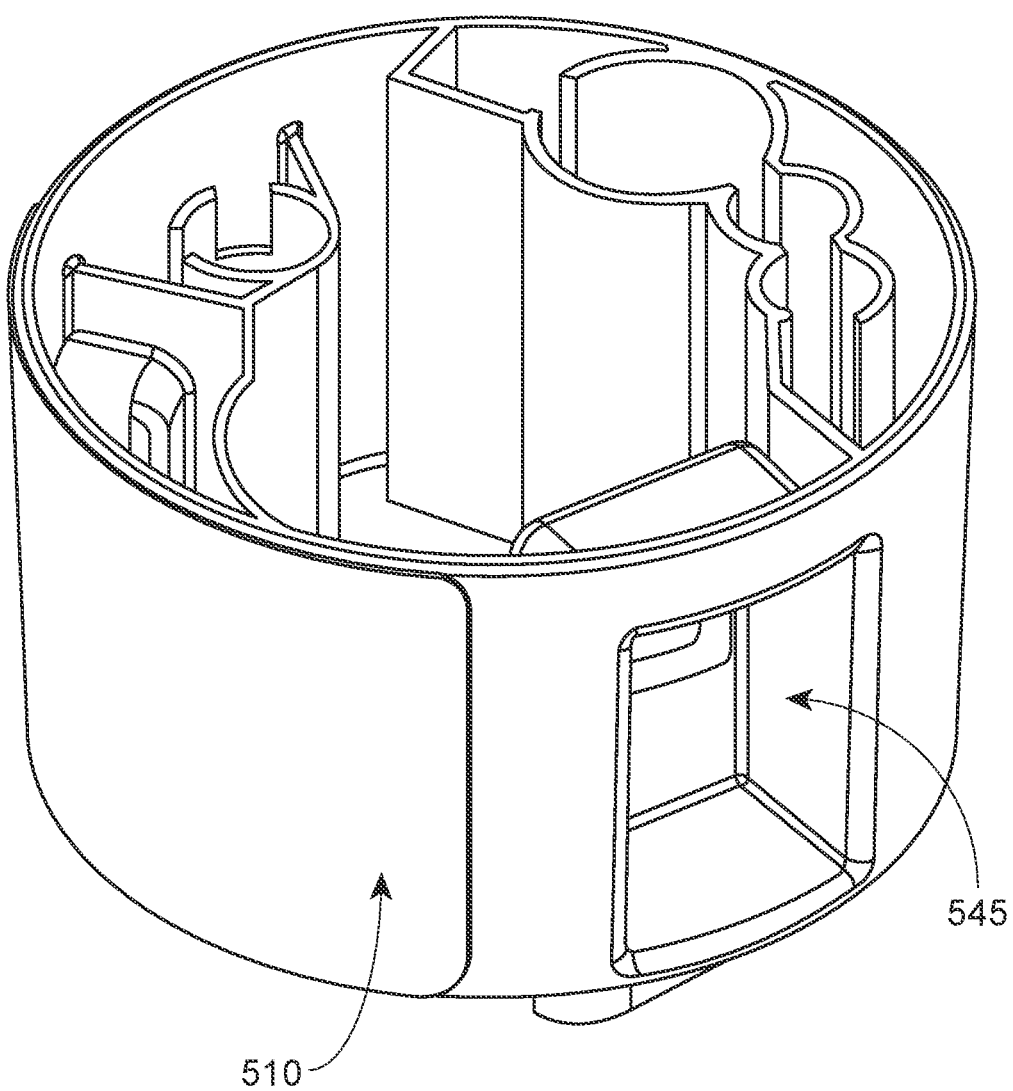
FIG. 1B shows a sample preparation cartridge with a cover positioned over the open side of the chambers according to one embodiment of the present disclosure.

A cylindrical structure according to one embodiment is shown in FIG. 1B. In this example, the cylindrical structure 500 is similar to the one shown in FIG. 1A. Also shown in FIG. 1B is a cover 510. The open sides of the chambers (not shown) are located on the exterior of the annular wall. As seen, the cover 510 curves to mate with the outside surface of the cylindrical structure 500 and fluidically seals the open sides of the chambers and the interconnections (not shown).

Figure 10:
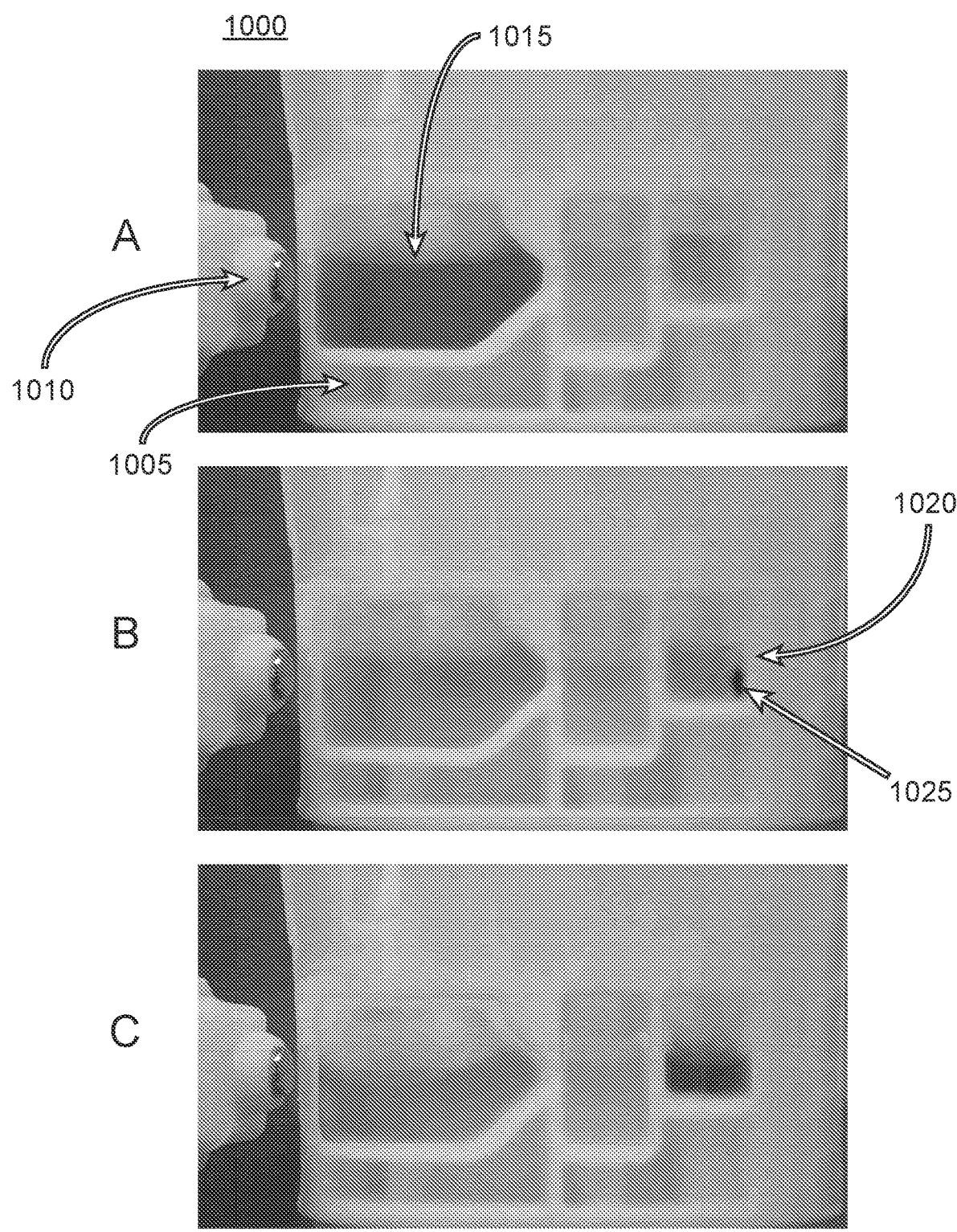
FIG. 10, Panels A, B and C, shows an illustration of a sample preparation cartridge rotating to a position to allow a magnet to be positioned proximal to the cover and magnetically capture paramagnetic particles in a chamber.

A cylindrical structure according to one embodiment of the present disclosure and similar to the cylindrical structure depicted in FIG. 1B is shown in FIG. 10. In this view, the cylindrical structure 500 and the cover 510 are broken out for illustration. In this example, the cylindrical structure 500 includes three cavities in the annular wall 530 that form a plurality of open-sided chambers 520 on the annular wall 530. As seen, the cover 510 curves to mate with the outside surface of the cylindrical structure 500 and fluidically seals the open sides of the chambers 520 and the interconnections.

Figure 1C:
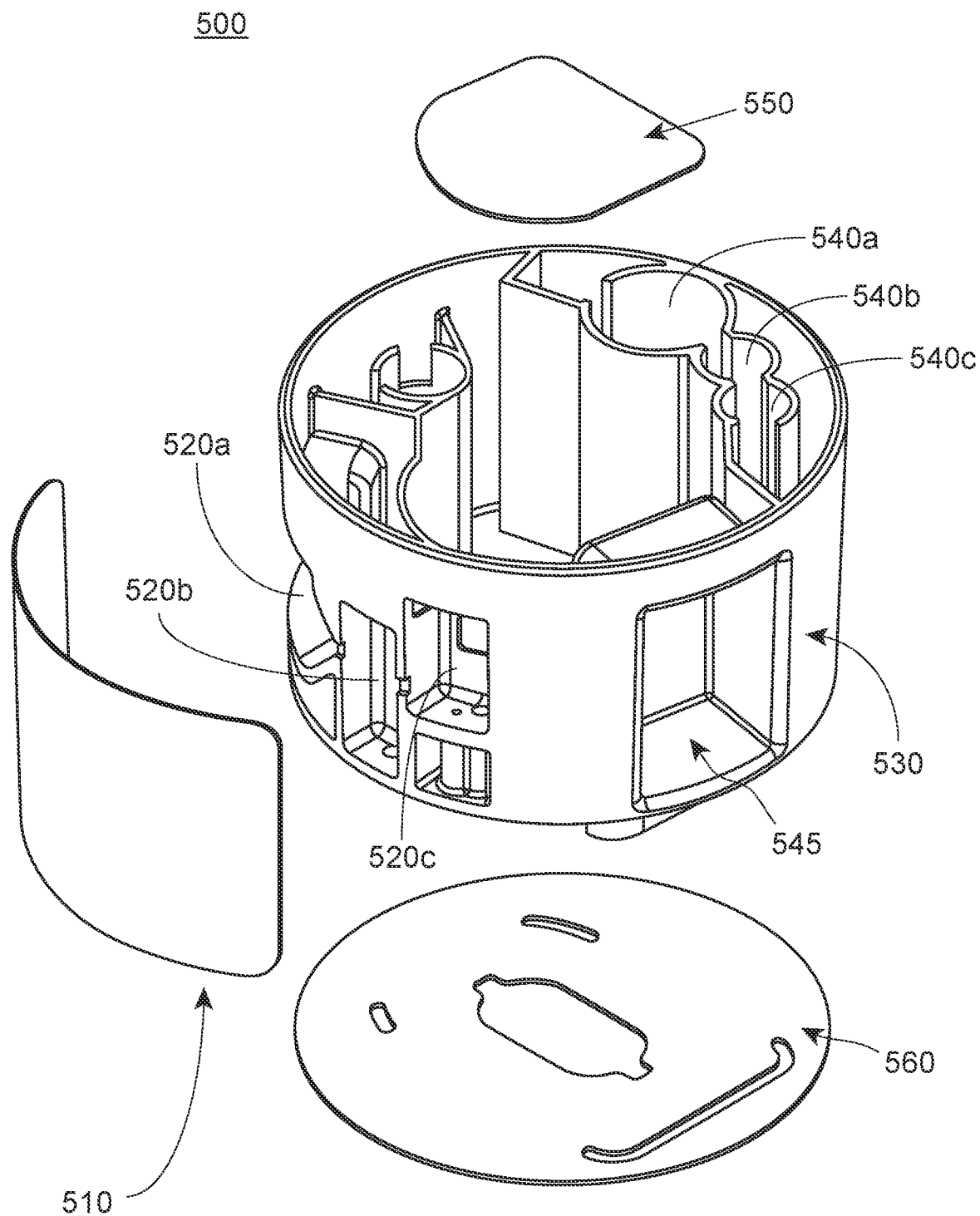
FIG. 1C shows an exploded view of a cylindrical structure with a cover similar to that depicted in FIG. 1B and two sealing covers according to one embodiment of the present disclosure.

Also visible in FIGS. 1A-1C are indentations 445 and 545. These indentations may serve as a housing for additional functionalities. For example, the indentation may house a bar code or a QR code. The code may be directly printed on the cartridge or it may be printed on a substrate that is affixed on the cartridge. The code may be used to assign a unique identifier to the cartridge. The depth and position of the indentation may be matched to location of a code reader to ensure proper focus and alignment with the code reader.

FIG. 1C shows additional sealing films 550 and 560 that cooperate to provide top and bottom walls of channels 515a, 515b, and 515c connecting the chambers 520a, 520b, and 520c to individual wells 540a, 540b, and 540c in embodiments where wells are included in the cartridge 500. For example, the channels 515a, 515b, and 515c may be openings in a bottom wall of the cartridge which openings extends from bottom of a well to the vent/inlet of a chamber. The side walls of the opening are formed by the bottom wall while the top and bottom walls are provided by sealing films 550 and 560, respectively.

Figure 1D:
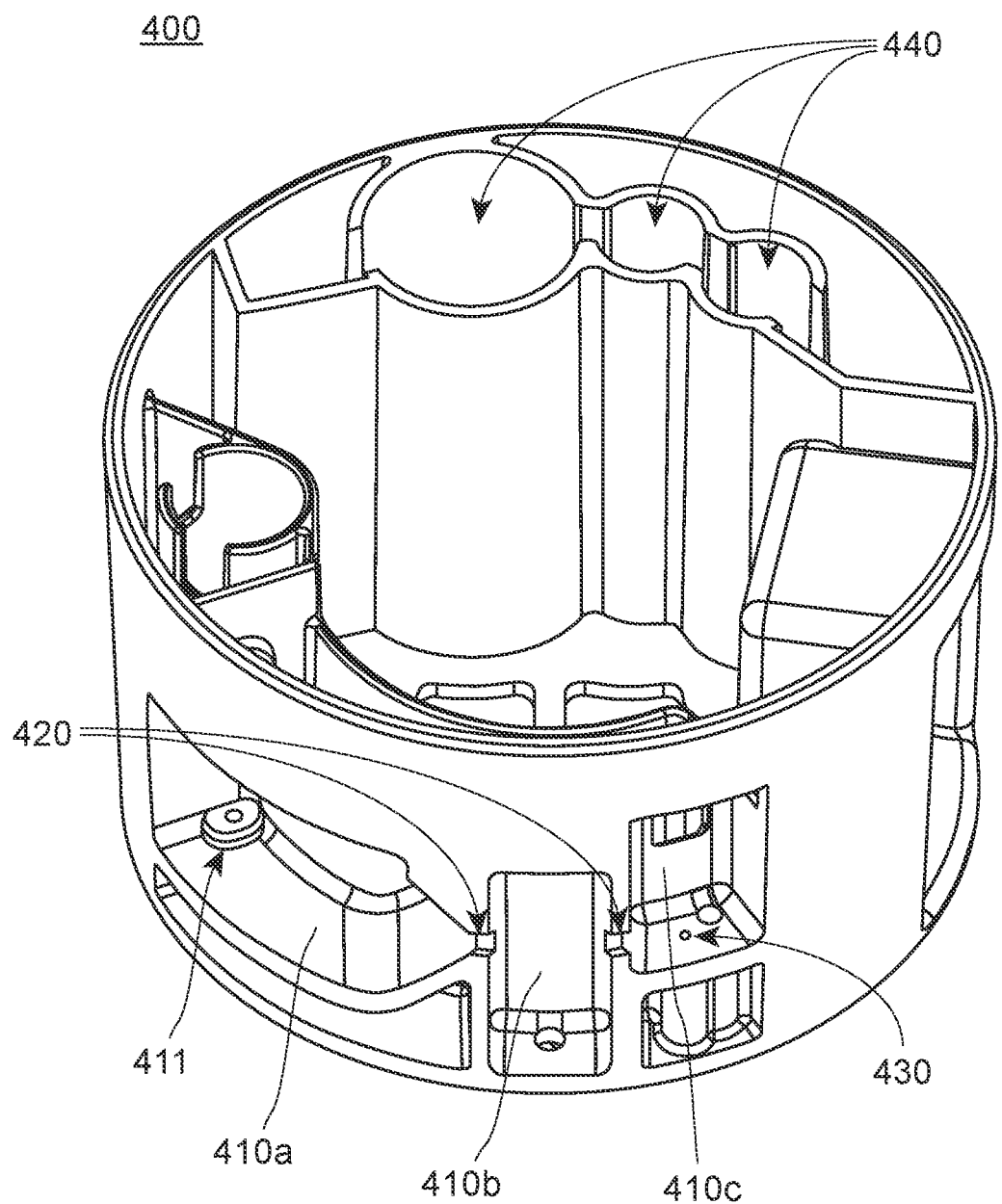
FIG. 1D shows a sample preparation cartridge in which one of the chambers include a compartment 411 for housing PMPs.

FIG. 1D shows an embodiment of a cartridge that includes a chamber 410a with a compartment 411 positioned on the bottom region. The compartment 411 comprises an opening fluidically connecting the compartment to the interior of the chamber. The compartment houses paramagnetic particles (PMPs) (not shown). During use of the cartridge, in some examples, a buffer disposed in the first chamber 410a may fill the compartment and the PMPs may flow into the chamber. In another example, a channel may be present underneath the compartment which is connected to a fluid pack of the buffer pack. The buffer pack (e.g., lysis buffer) may flow into the channel and flush the PMPs from the compartment into the chamber 410a.

In other embodiments, the cartridge may include a plurality of chambers that include an opening at a top region. An opening at the top region of the first chamber may be used to introduce a lysis buffer, PMPs, and sample in the first chamber. The second chamber may include air as an immiscible phase and may not include an opening (other than the interconnections to the first and third chamber). The second chamber may include oil as an immiscible phase and may include an opening in the top region for introducing oil into the second chamber. The third chamber may include an opening for introducing an elution buffer in the third chamber. This opening in the third chamber may also be utilized for removing the elution buffer or a portion thereof for analysis (e.g., PCR).

Buffer Pack

In certain embodiments, sample preparation cartridges may include a buffer pack. A buffer pack may comprise one or more fluid packs. Each fluid pack may contain a fluid. The fluid packs may contain any convenient fluid in any convenient amount. In some embodiments, fluid packs may comprise each of a lysis buffer pack, an immiscible phase pack and an elution buffer pack. In some embodiments, fluid packs may comprise a lysis buffer pack and an elution buffer pack. In certain embodiments, the immiscible phase may comprise an oil. In certain embodiments, the immiscible phase may comprise air. In some instances, one or more of the fluid packs may further comprise PMPs. The fluid pack may contain any convenient amount of PMPs, measured based on, for example, the volume or the weight of PMPs. For example, the PMPs may be mixed with a fluid when included in a fluid pack. In some instances, PMPs may be included in a fluid pack that comprises a lysis buffer.

In certain embodiments, the buffer pack is configured to fit within the wells of the cylindrical structure. For example, when the wells are shaped as substantially hollow cylinders, the buffer pack may be shaped as cylinders that fit within the wells of the cylindrical structure.

In some embodiments, the lysis buffer can be formulated to release nucleic acid from a broad spectrum of samples, such as tissue samples, cells, viruses, or body fluid samples. The lysis buffer can also be designed to lyse all types of pathogens, such as viruses, bacteria, fungi, and protozoan pathogens. Such lysis buffer can contain a chaotropic agent, particularly, guanidine hydrochloride.

Figure 4A:
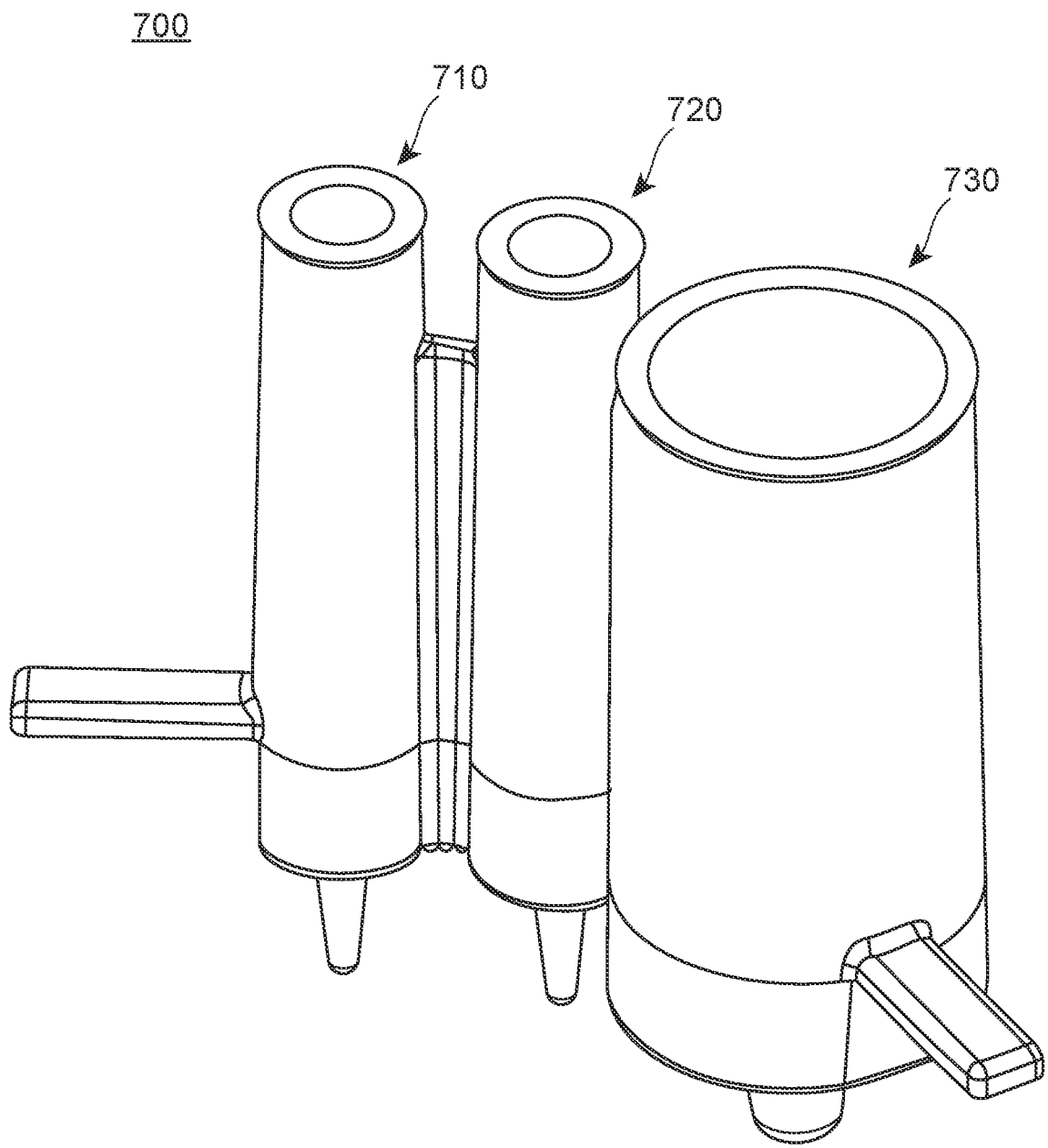
FIG. 4A shows a buffer pack according to one embodiment of the present disclosure.

A buffer pack according to one embodiment of the present disclosure is shown in FIG. 4A. As seen, the buffer pack 700 in this example is comprised of cylindrical structures 710, 720, and 730 such that the buffer pack can hold fluid packs (not shown). In embodiments where the second chamber comprises air as the immiscible phase, the buffer pack may not include a pack comprising oil.

Figure 4B:
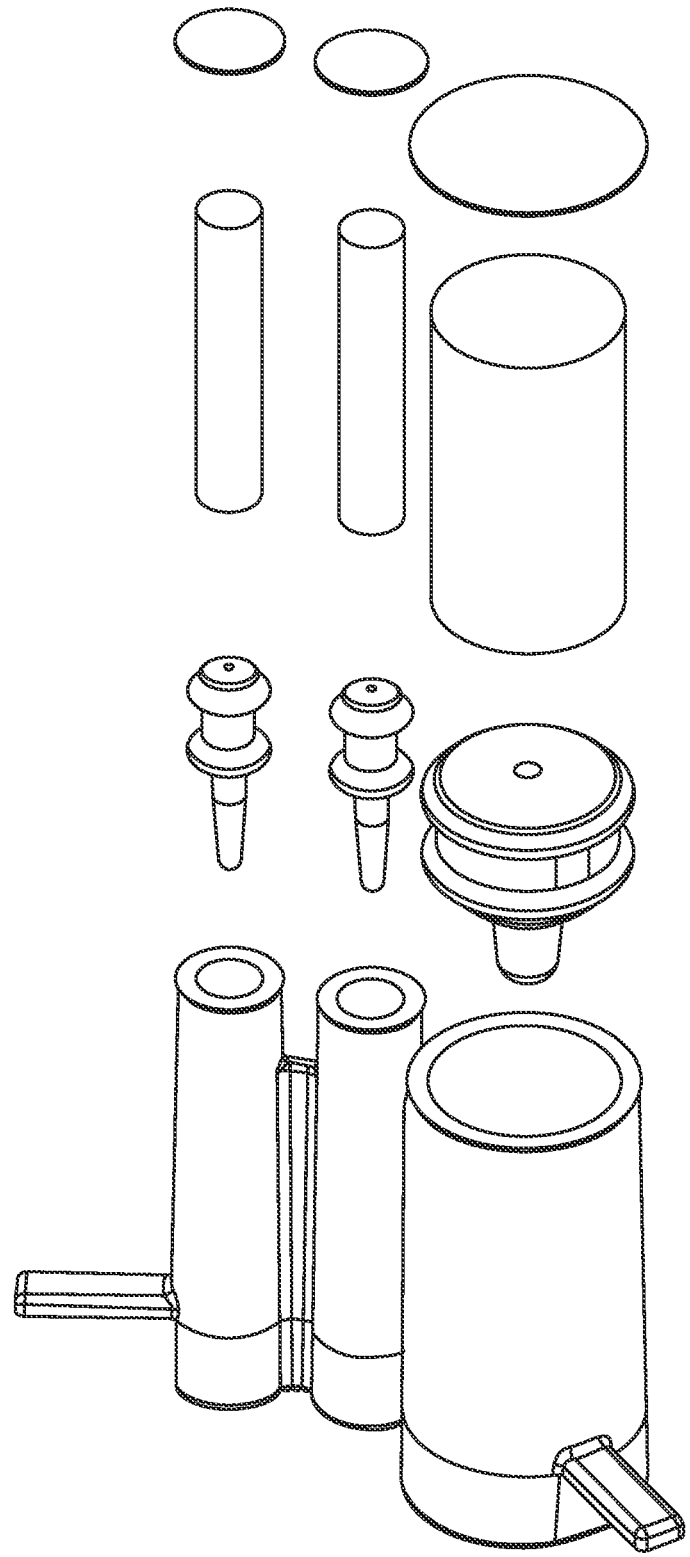
FIG. 4B shows an exploded view of a buffer pack similar to that depicted in FIG. 4A according to one embodiment of the present disclosure.

A buffer pack according to one embodiment of the present disclosure and similar to the buffer pack depicted in FIG. 4A is shown in FIG. 4B. In this figure, internal components of the buffer pack are broken out for illustration.

The buffer pack may be inserted into the wells 440 (see FIG. 1A) in the cylindrical structure 400. The buffer pack may be actuated to release fluids contained therein which travel to the corresponding chambers 410a, 410, and 410c (see FIG. 1A). In some examples, cylindrical structure 710 of buffer pack 700 contains a lysis buffer and is fluidically connected to the first chamber 410a; cylindrical structure 720 contains oil or a wash buffer and is fluidically connected to the second chamber 410b; and cylindrical structure 730 contains elution buffer and is fluidically connected to the third chamber 410c.

Sealing Lid Assembly

As noted above, the sample preparation cartridges disclosed herein include a cylindrical structure that includes a top end, a bottom end and an annular wall extending between the top and bottom ends. In certain embodiments, a sealing lid assembly covers the top end of the cylindrical structure. The sealing lid assembly may include a sealing plate and a protective cover. The sealing plate is positionable on top end of the cylindrical structure. The protective cover is positionable over the sealing plate. The protective cover is sized to enclose the periphery of the sealing plate and snap on and around the top end of the cylindrical structure to keep the sealing plate in place.

The sealing plate is sized to fit on the top end of the cylindrical structure and close the top end. In certain embodiments, the sealing plate may include an opening aligned with an opening in the third (elution) chamber for removing elution buffer for analysis of eluted nucleic acid. In other embodiments, the sealing plate may further include a plunger assembly. The plunger assembly may include a gasket seal mounted on a shaft, a spring, and a trigger that engages the spring and the shaft. The shaft may be any convenient length, such as a length that is less than or equal to the height of a corresponding chamber. The gasket seal may be shaped so that the size of the operative end of the gasket seal is substantially similar to the corresponding chamber with which the plunger is integrated. In these embodiments, the spring may apply tension to the plunger in a retracted position. That is, when the plunger is retracted, the spring is under tension. By retracted, it is meant that the gasket seal end of the plunger is retracted. When in the retracted position, the plunger may not plunge fluid from a corresponding chamber. The amount of tension applied by the spring when the plunger is retracted corresponds to the amount of tension applied by the spring to the plunger when the plunger is no longer retracted and may vary as desired. By a trigger that engages the spring and the shaft, it is meant that the trigger may control the release of a spring under tension holding the plunger in a retracted position.

In certain embodiments, the trigger and the spring are mechanically interlocked so that the trigger is armed when the plunger is in the retracted position. By armed, it is meant that depressing the trigger releases tension on the spring, thereby causing the plunger to move from the retracted position to the plunged position.

In these embodiments, the gasket seal of the plunger may be positioned to engage with one of the chambers. By engaging with one of the chambers, it is meant that the plunger assembly is positioned so that when the plunger assembly is in the plunged position, the gasket seal of the plunger nearly fills the bottom portion of the chamber, and when the plunger assembly is in the retracted position, the gasket seal of the plunger does not fill the bottom portion of the chamber. That is, the movement of the plunger from a retracted to a plunged position is such that the plunger may plunge the chamber. By plunging the chamber, it is meant that as the plunger transitions from a retracted to a plunged position, the gasket seal of the plunger engages with the chamber to apply pressure to any fluid in the chamber.

In these embodiments, the trigger may be positioned on the sealing lid assembly so that the trigger protrudes a distance beyond the outside wall of the cylindrical structure. By protruding a distance beyond the outside wall of the cylindrical structure, it is meant that the distance between the axis of the cylindrical structure and the furthest point on the trigger is greater than the distance between the axis of the cylindrical structure and the outside edge of the annular wall. The trigger may protrude any convenient distance beyond the outside edge of the annular wall. In these embodiments, the trigger may be oriented to be depressed in a lateral direction. By depressing the trigger, it is meant activating the trigger to release tension on the spring, to which the trigger is mechanically interlocked. By oriented to be depressed in a lateral direction, it is meant that the trigger is positioned so that, in order to depress the trigger, the trigger must be moved in a substantially lateral direction.

Components of a sample preparation cartridge according to one embodiment of the present disclosure is shown in an exploded view in FIG. 2. In this view, the cylindrical structure 210 and the protective cover 220 are broken out for illustration. Also, in this example, the sample preparation device includes a buffer pack 230 and a sealing lid assembly 240. Components of the sealing lid assembly 240, including the plunger 250, the spring 260 and the trigger 270, are also shown. Two PCR tubes 211 are provided for collecting the eluted nucleic acid. PCR tube retaining cap 213 snaps into the bottom region of the cartridge.

Figure 3:
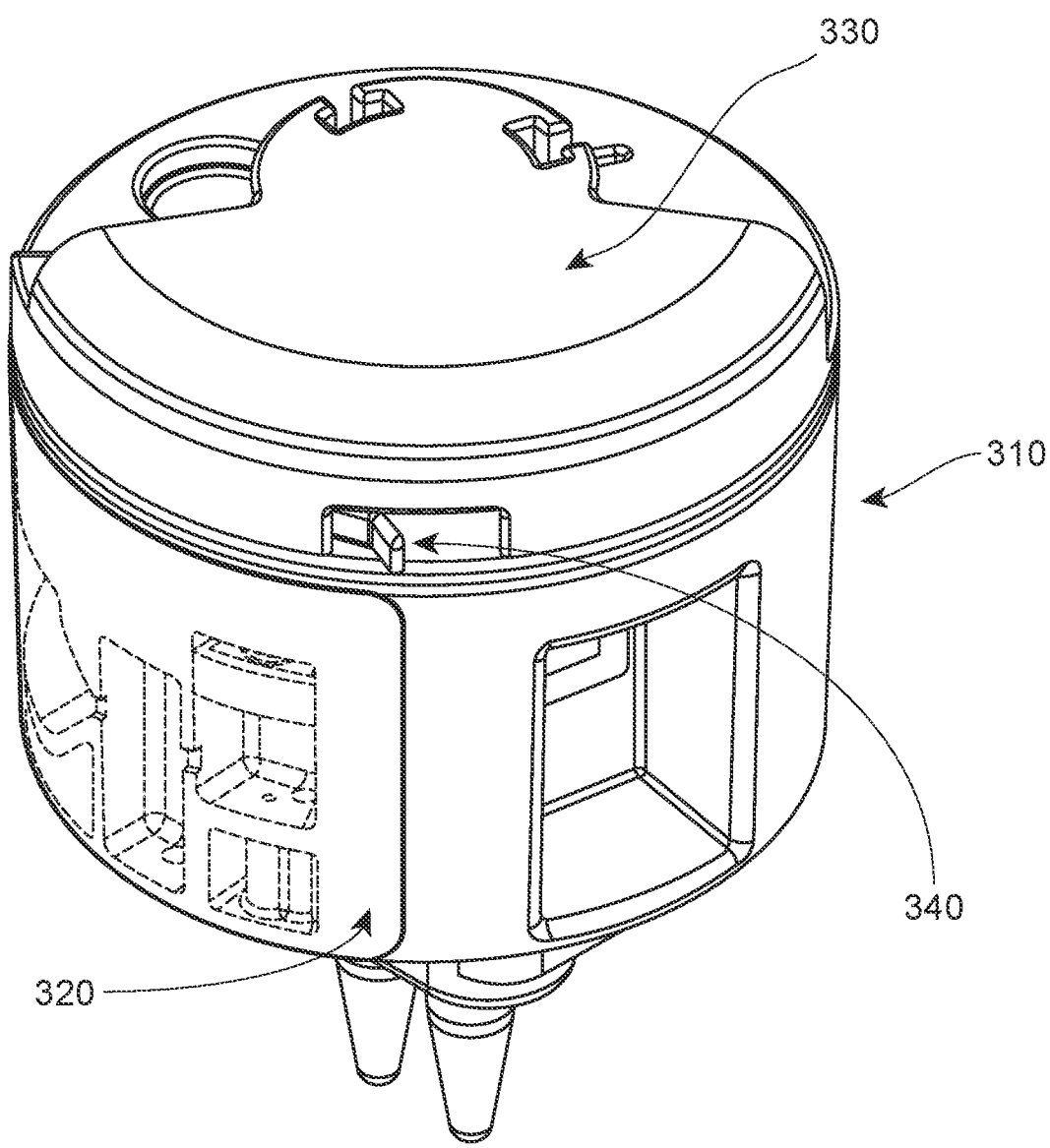
FIG. 3 shows a cartridge with a protective cover. The trigger of the plunger assembly is also shown.

A sample preparation cartridge according to one embodiment of the present disclosure is shown in FIG. 3. In this example, the sample preparation device 300 includes a cylindrical structure 310, a cover 320, a protective cover 330, and a trigger 340. In this illustration, it is seen that the trigger 340 protrudes a distance beyond outer surface of the annular wall of the cylindrical structure 310.

Figure 8:
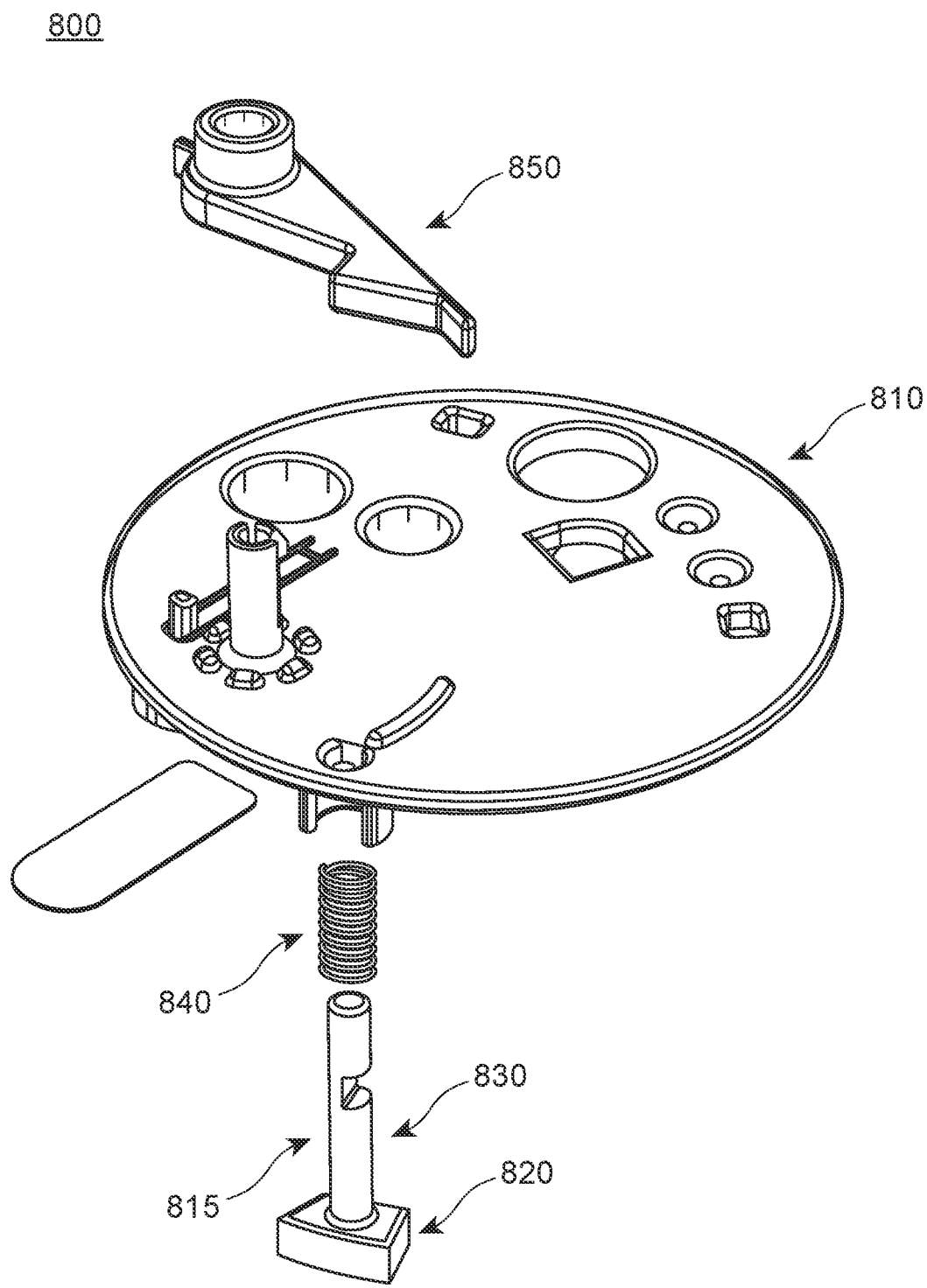
FIG. 8 shows an exploded view of the sealing plate assembly according to one embodiment of the present disclosure.

A sealing lid assembly according to one embodiment of the present disclosure is shown in FIG. 8. In this example, the sealing lid assembly 800 includes a sealing plate 810, a plunger 815 comprising a gasket seal 820 mounted on a shaft 830, a spring 840 and a trigger 850. As seen, the shaft 830, spring 840 and trigger 850 are positioned so that the trigger 850 engages the spring 840 and the shaft 830 and the spring 840 applies tension to the plunger 815 in a retracted position. It is also seen in this example that the trigger 850 protrudes a distance beyond the outside wall of the protective cover 140 (not shown) and the trigger 850 is oriented to be moved in a lateral direction.

Cap

As summarized above, in certain embodiments, the sample preparation cartridge further includes a cap slidably positioned on the top of the cylindrical structure. By slidably positioned, it is meant that the cap can be positioned on the top of the cylindrical structure in such a manner that it is can slide towards the cylindrical structure.

In certain embodiments, caps may comprise one or more arms positioned to mechanically engage the buffer pack. For example, the cap may be shaped substantially flat where one or more arms are attached to one flat side of the cap. Such arms may be any convenient size or shape. For example, the length of the arms may be long enough so that when the cap is positioned on top of the cylindrical structure, the arms can reach wells on the inside of the cylindrical structure.

In certain embodiments, the cap may include a plunger positioned such that when the cap is slid into the cylindrical structure the plunger enters a sample chamber and expels the sample to the lysis chamber. The sample chamber may be adjacent the first (lysis) chamber and connected to the lysis chamber via a channel. One of the arms of the cap may enter the lysis buffer pack forcing the lysis buffer out of the pack and into the first (lysis) chamber. Another arm of the cap may enter the immiscible phase pack, if present, and push the oil into the second (immiscible phase) chamber while a third arm of the cap enters the elution buffer pack and pushes the elution buffer into the third (elution) chamber.

A cartridge may be loaded into an instrument fitted with a magnet where the magnet is positioned with respect to the cartridge such that it can be used to move PMPs from the lysis chamber through the immiscible phase chamber into the elution chamber. The instrument may include a motor that engages the cartridge to rotate the cartridge relative to the magnet or the magnet may be configured to move along the annular surface of the cartridge.

Sample Input Component

In certain embodiments, sample preparation cartridges further include a sample input component positioned on the protective cover. Sample input components may be used to insert a sample, e.g., a biological sample into the sample preparation device. In particular, the sample may be loaded from the sample input component into a chamber of the sample preparation device.

Sample Preparation Systems

As summarized above, sample preparation systems include a cylinder housing in which the sample preparation sample preparation cartridge can be removably disposed. By removably disposed, it is meant that the cylindrical structure can be fit into the cylinder housing in such a manner that the cylindrical structure can nonetheless be separated from the cylinder housing. For example, a user may dispose the cylindrical structure in the cylinder housing and may remove the cylindrical structure from the cylinder housing after sample preparation. As summarized above, the cylinder housing includes a magnet. By magnet, it is meant any object having the ability to produce a magnetic field external to itself. For example, the magnet may produce a magnetic field capable of attracting paramagnetic particles. In some instances, the magnet may be an electromagnet. In certain embodiments, the magnets are positioned proximal to the exterior of the annular wall. In some embodiments, the magnet is external to the cylindrical housing and is used to transfer the magnetic particles between chambers of the cylindrical housing.

In certain embodiments, the cylindrical structure rotates within the cylinder housing. By rotate, it is meant that the cylinder housing permits the cylindrical structure freedom to rotate, for example, around the axis of the cylindrical structure formed by connecting the center of the top end with the center of the bottom end of the cylindrical structure. In other embodiments, the cylindrical structure maintains a fixed position in space and the cylinder housing rotates around the cylindrical structure.

In certain embodiments, a reusable magnet is used to process samples using a disposable consumable cylinder structure in a sample processing instrument. The use of the reusable magnet would reduce the waste with each consumable.

Figure 5A:
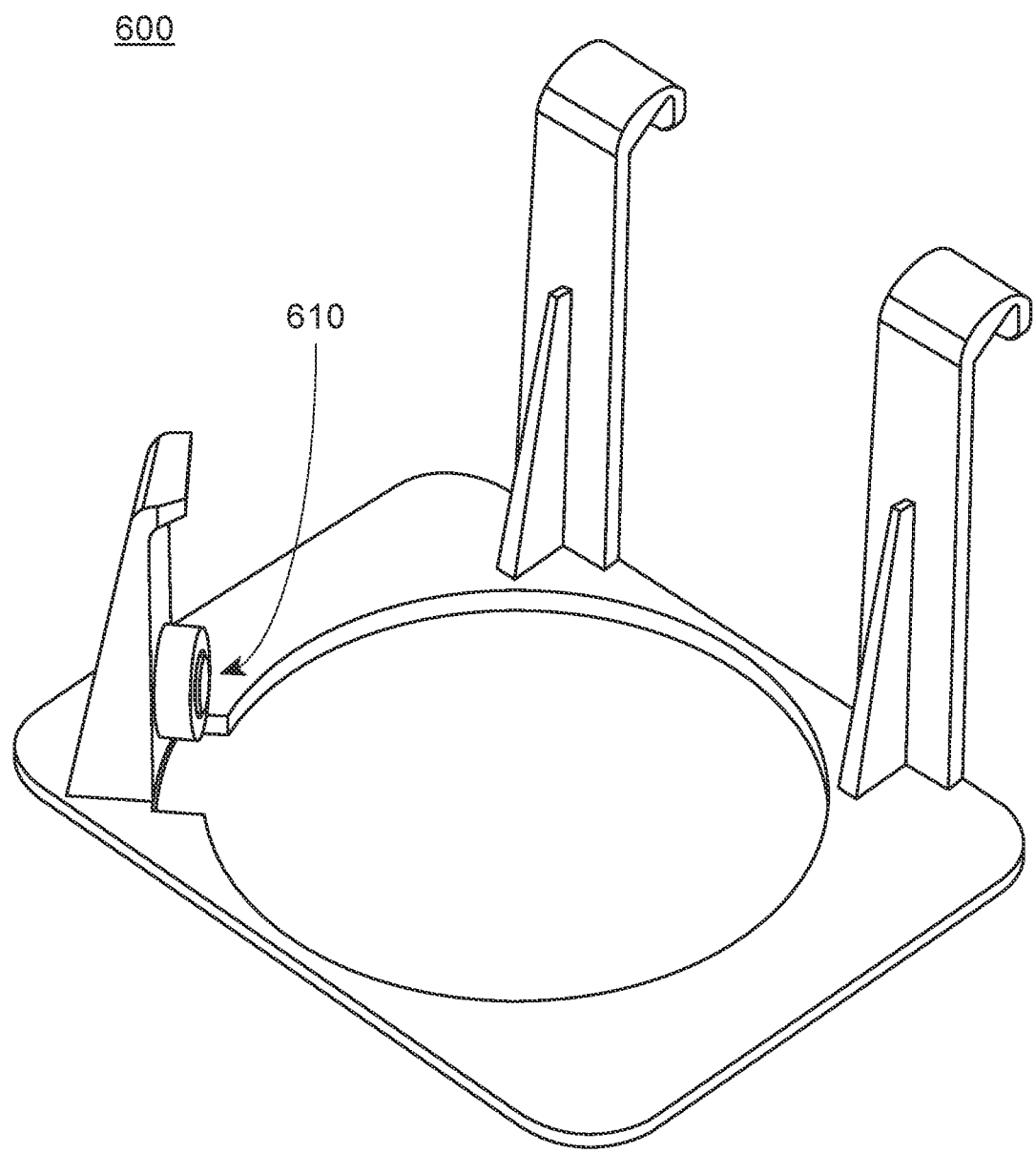
FIG. 5A shows a cylinder housing according to one embodiment of the present disclosure.

A cylinder housing according to one embodiment of the present disclosure is shown in FIG. 5A. In this example, the cylinder housing 600 includes a magnet 610. As seen, the magnet is located on the cylinder housing such that, when a cylindrical structure is disposed into the cylinder housing 600, the magnet 610 is positioned proximal to the exterior of the annular wall of the cylindrical structure. In some embodiments, the magnet 610 is external to the cylindrical housing and is used to transfer the magnetic particles between chambers of the cylindrical housing.

Figure 5B:
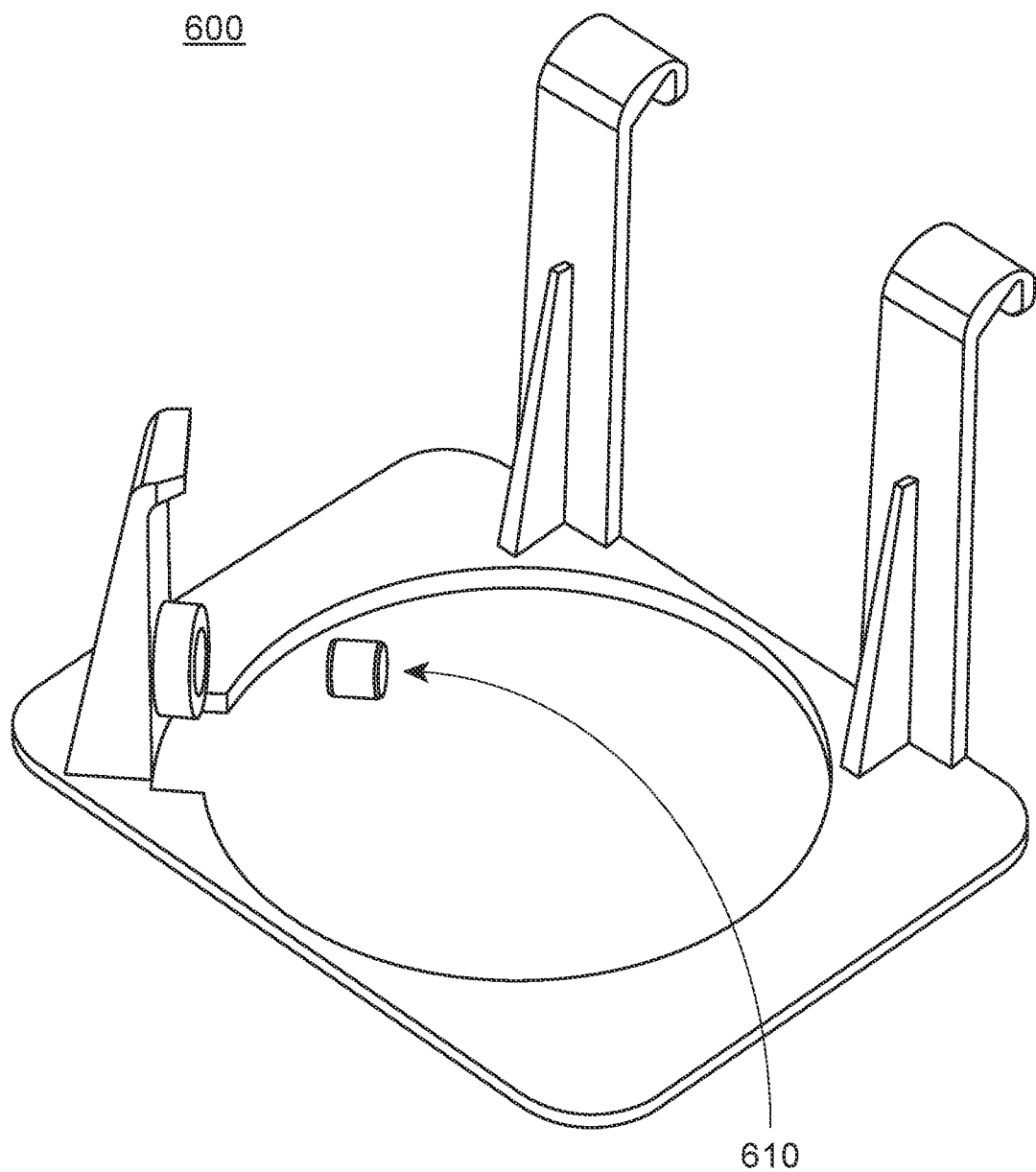
FIG. 5B shows an exploded view of a cylinder housing similar to that depicted in FIG. 5A according to one embodiment of the present disclosure.

A cylinder housing according to one embodiment of the present disclosure and similar to the cylinder housing depicted in FIG. 5A is shown in FIG. 5B. In this view, the cylinder housing 600 and the magnet 610 are broken out for illustration.

Figure 6:
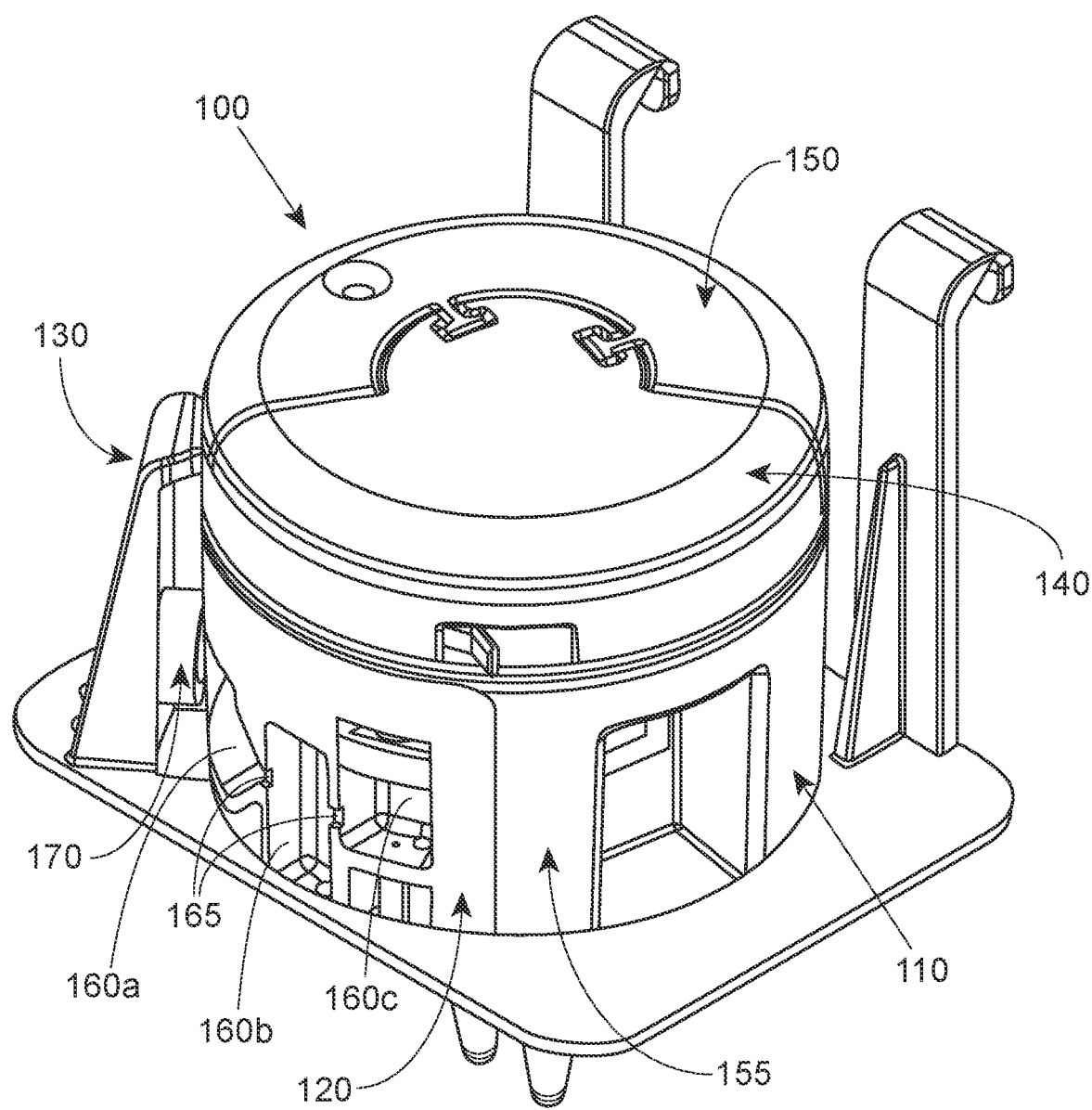
FIG. 6 shows a sample preparation system according to one embodiment of the present disclosure. In this example, the cartridge includes first, second and third chambers on the annular wall. Each is interconnected to a proximal chamber by channels that are recesses in the annular wall. The cartridge is disposed in the cylinder housing and the magnet is positioned adjacent the annular wall.

A sample preparation system that includes a sample preparation cartridge 100 and a cylinder housing 130, according to one embodiment of the present disclosure is shown in FIG. 6. In this example, the sample preparation cartridge 100 includes a cylindrical structure 110, a cover 120, a protective cover 140, and a cap 150. Also depicted in the figure are the annular wall 155 of the cylindrical structure and three cavities in the annular wall that form three open-sided chambers 160a, 160b, and 160c on the annular wall. As seen in the figure, the open side of each chamber 160a, 160b, and 160c is oriented towards the outside of the cylindrical structure 110. In addition, the open sides of the chambers 160a, 160b, and 160c are enclosed by the cover 120. In FIG. 6, cover 120 is depicted as transparent to aid visualization of the chambers 160a, 160b, and 160c but cover 120 need not be transparent. The cover 120 curves to mate with the outside surface of the annular wall 155, and fluidically seals the open sides of the chambers. Also seen in this figure are interconnections 165 between the chambers 160a, 160b, and 160c. As seen in the figure, the interconnections 165 are channels that are recesses in the annular wall between chambers. The figure also depicts the magnet 170 in the cylinder housing 130. As seen, the magnet 170 is positioned proximal to the exterior of the annular wall 155 of the cylindrical structure 110.

Figure 7:
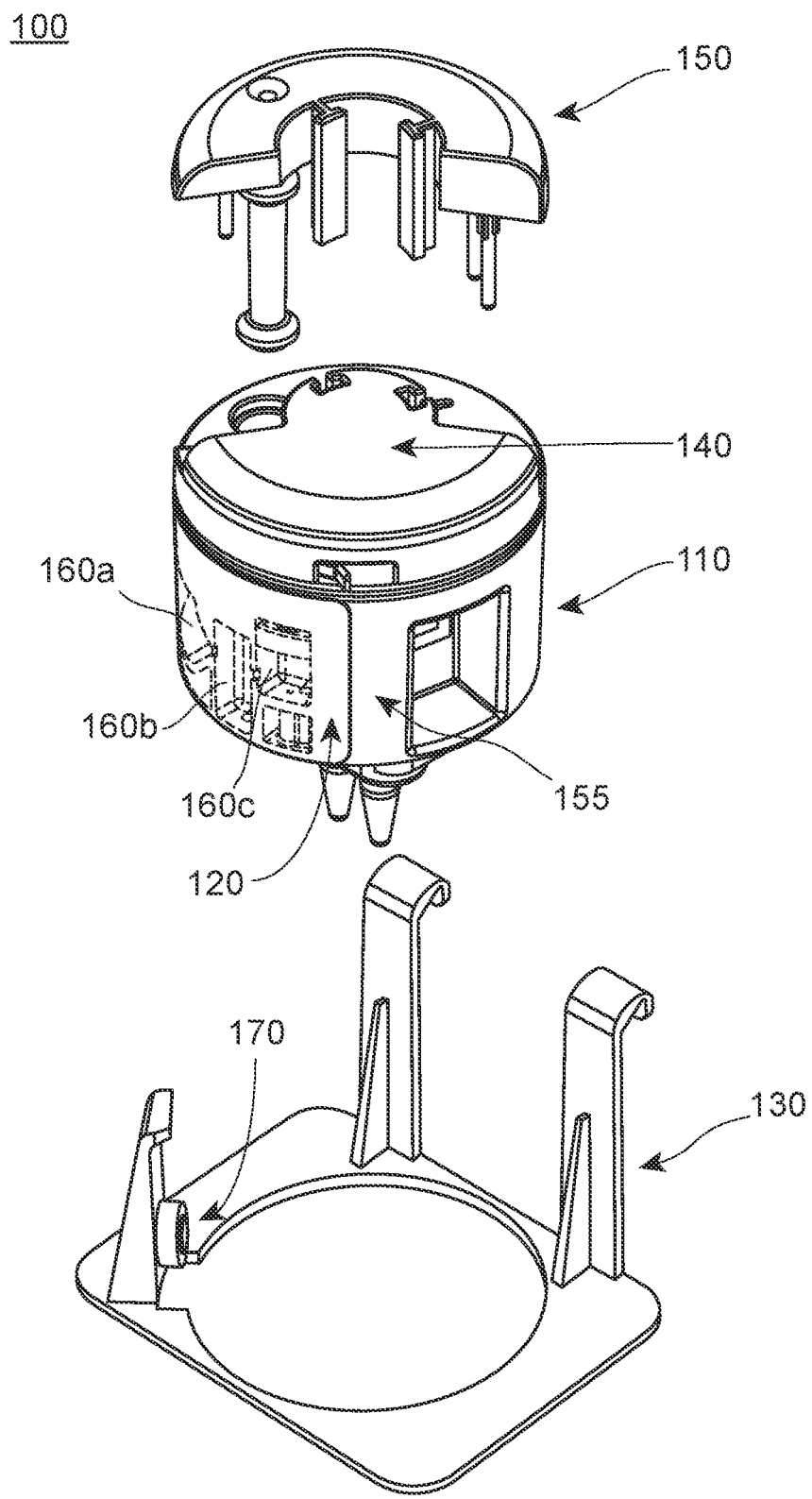
FIG. 7 shows a sample preparation system similar to that depicted in FIG. 6 in an exploded view. In this view, the cylinder housing, the cartridge sealed with the protective cover and the cap are broken out for illustration.

A sample preparation device according to one embodiment of the present disclosure and similar to the sample preparation device depicted in FIG. 6 is shown in FIG. 7. In this view, the cylinder housing 130, the sample preparation cartridge 110, and the cap 150 are broken out for illustration.

Figure 9:
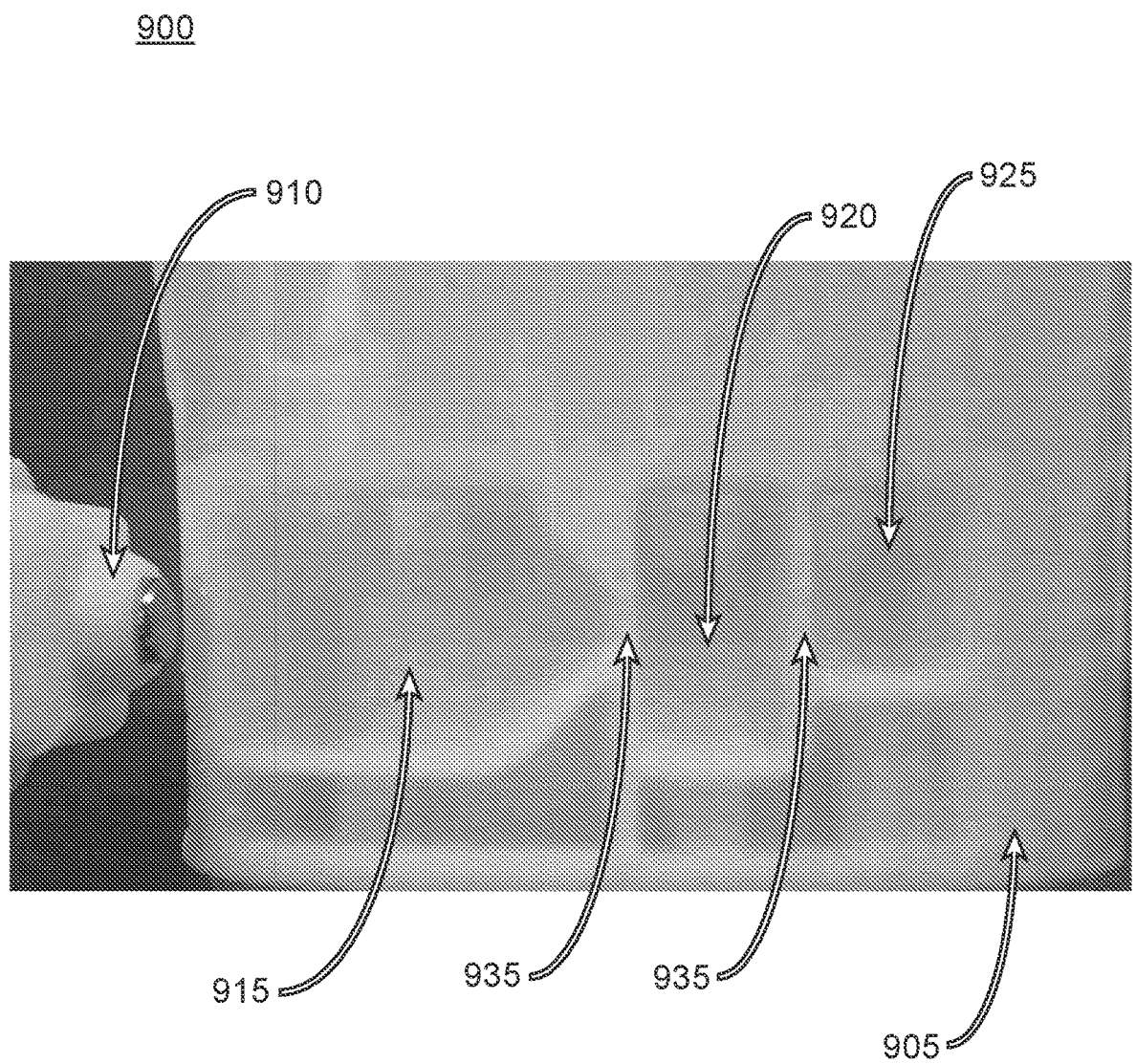
FIG. 9 shows an illustration of a sample preparation cartridge rotating to a position to allow a magnet to be positioned proximal to the cover and magnetically capture paramagnetic particles in a chamber.

FIG. 9 shows an illustration of a sample preparation cartridge rotatable to a position to allow a magnet to be positioned proximal to the cover and magnetically capture paramagnetic particles in a chamber. Shown are a sample preparation system 900 including a sample preparation cartridge 905 and a magnet 910. The sample preparation cartridge includes a first chamber 915 with a lysis buffer as well as, in some instances, paramagnetic particles to which nucleic acids can bind and a sample comprising cells, virus, and/or nucleic acid, a second chamber 920 with an immiscible phase (e.g., oil or air), and a third chamber 925 with an elution buffer. The sample preparation cartridge 905 further includes a first recess 935 in the annular wall interconnecting the first chamber 915 with the second chamber 920 and a second recess 935 in the annular wall interconnecting the second chamber 920 and the third chamber 925. The magnet 910 is used to transfer the magnetic particles between chambers of the sample preparation cartridge.

FIG. 10 illustrates the transfer of PMPs from a first chamber to a third chamber of a sample preparation cartridge using a magnet. In the initial stage of sample preparation, a sample is contacted with a lysis buffer and PMPs in the first chamber 1015. The PMPs are dispersed as indicated by the dark color of the solution in the first chamber 1015.

The sample preparation cartridge can be rotated to place different regions of the cartridge adjacent the magnet. Alternatively, the magnet can be positioned adjacent different regions of the cartridge by moving the magnet. Positioning a magnet 1010 adjacent the first chamber results in aggregation of the PMPs which can be transferred to the third chamber through the second chamber by relative movement between the magnet and the cartridge. Panel B shows an aggregate of paramagnetic particles 1025 in the third chamber 1020. In Panel C, the dark color of the solution in the third chamber 1020 illustrates that paramagnetic particles are mixed in the elution buffer in the third chamber 1020.

Automation for the Methods of Using the Sample Preparation Cartridges

Certain embodiments also provide sample preparation cartridges that can be actuated using a motor. The motor can be automated thereby automating the methods of using the sample preparation cartridges disclosed herein. The motor can also be controlled by a computer program, which when executed by a processor, causes the motor to perform the methods of using the devices disclosed herein.

In certain embodiments, the motor rotates the cylindrical structure in the increments of 1.8° angle.

In some embodiments, the motor rotates the cylindrical structure to return it to a predetermined position, for example, where the magnet is positioned proximal to the first chamber, second chamber, or third chamber.

The motor can be configured to provide only a fraction of the full 360° rotation. For example, the motor can be configured to provide only between 60° and 120° rotation, preferably, between 80° and 110° rotation, even more preferably, between 90° and 100° rotation, and most preferably, about 90° rotation.

Figure 11:
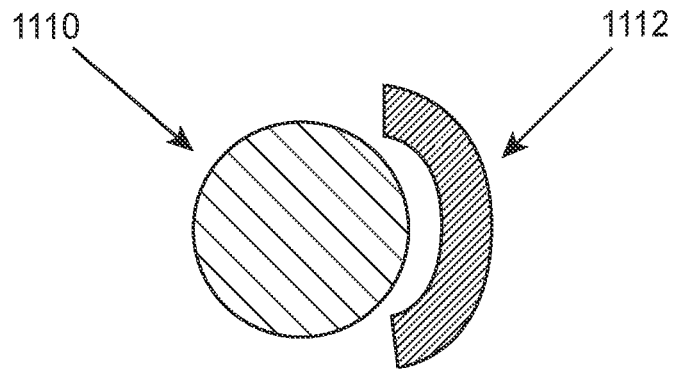
FIG. 11 shows an example of a motor that can automate the methods of using the sample preparation cartridges disclosed herein.

The motor assembly can comprise a rotary component 1110 comprising a holder for the sample preparation cartridge that is positioned adjacent a stationary component 1112 which holds a magnet, as shown in FIG. 11.

In some embodiments, the motor can further facilitate mixing of the contents of the sample preparation cartridge. Such mixing can be performed by motor mediated shaking of the sample preparation cartridge. Appropriate mixing can be provided by the control of start position, amplitude, and/or speed of shaking. Mixing may reduce sample preparation time and/or improve sample preparation by reducing non-specific binding and improving homogenous mixing.

Representative Embodiments

The devices having been generally reviewed, representative specific embodiments of various device configurations and constituent components thereof are now described in greater detail.

Figure 12:
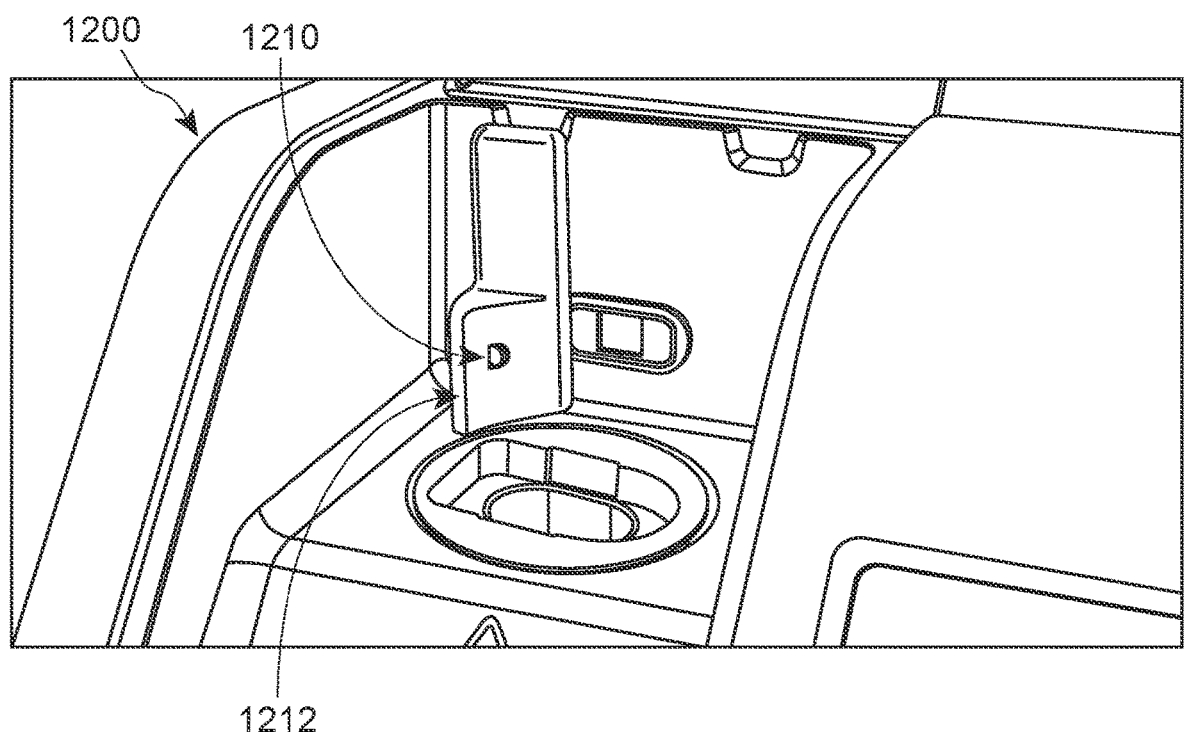
FIG. 12 shows a reusable magnet that could be used repeatedly for processing samples using disposable sample preparation cartridges. The reusable magnet can be placed in a sample processing device and can be used to process a plurality of cartridges thereby avoiding the need to use separate magnets for each disposable cartridge.

FIG. 12 shows a sample processing instrument 1200 configured to process a sample using a disposable sample preparation cartridge disclosed herein. The sample processing instrument is fitted with a reusable magnet 1210. The reusable magnet is mounted on a support 1212 and placed on the instrument in a manner that the magnet is proximal to the cover of the sample preparation cartridge and can be used to move magnetic particles between different chambers of a disposable sample preparation cartridge by rotation of the sample preparation cartridge.

Figure 13:
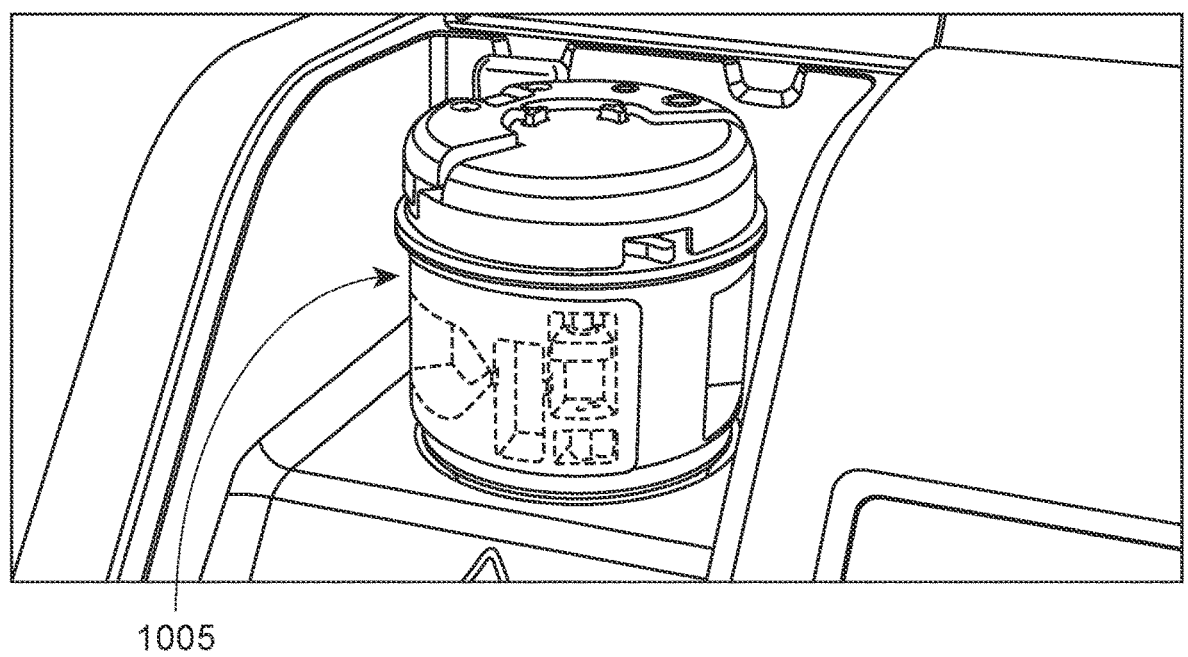
FIG. 13 shows an example of a disposable sample preparation cartridge placed in a sample processing instrument such that the magnet is positioned proximal to the annular wall of the cartridge.

FIG. 13 shows a disposable sample preparation cartridge placed in the sample processing instrument such that the magnet is situated adjacent the sample preparation cartridge. In the embodiment depicted in FIGS. 12 and 13, the magnet is stationary during sample preparation while the cartridge rotates about a central axis. The rotation of the cartridge places a chamber of the cartridge in proximity to the magnet.

Additional Functionalities Added to the Sample Preparation Device

In certain embodiments, the sample preparation device comprises additional functionalities that can monitor certain aspects of the sample and/or the methods of using the devices.

For example, the sample preparation device can comprise a temperature sensor that can monitor and report the temperature of the reagents, particularly, in various chambers of the sample preparation device. The sample preparation device may be provided with the means for controlling the temperature, such as heaters or coolers that can provide a desired temperature in one or more chambers of the sample preparation device.

The sample preparation device can be fitted with a fluorometer for reading fluorescence in one or more chambers of the sample preparation cartridges. The fluorometer can be configured to provide an on-demand reading with specific parameters, preferably, without any movement caused by the motor, if present.

In further embodiments, the sample preparation device can be fitted with a camera for capturing images during the process of sample preparation. One or more cameras can be positioned or configured to capture images from one or more chambers of the device.

The devices disclosed herein are suitable for methods of detection of nucleic acids in a short amount of time, such as less than 20 minutes, less than 15 minutes, less than 10 minutes, or less than 5 minutes. For example, the nucleic acids isolated from a sample using the sample preparation device may be transferred to a collection chamber, e.g., one or more PCR tubes that are in fluidic communication with the third chamber. See, e.g., FIG. 2 depicting PCR tubes 211 that are in fluidic communication with the third chamber 410c (see FIG. 1A). An elution buffer can be used to elute nucleic acids from PMPs in the third chamber 410c. The elution buffer comprising the nucleic acids can be drained into the PCR tubes 211 via the drain hole 430. Plunger 250 (see FIG. 2) can be used to push the elution buffer through the drain hole 430. The eluted nucleic acids can be further analyzed by, for example, an amplification reaction, such as, PCR.

In some cases, the cartridges and associated instrumentation are configured so that a sample can be loaded and the rest of the processing steps are automated. Thus, the results can be obtained with minimal user mediated steps. Particularly, the user may only need to load the sample in the cartridge and load the cartridge into the instrumentation, not necessarily in that order, and actuate the analytical instrument to analyze the sample. The instrumentation is configured to process the sample to isolate the nucleic acids from the sample; deliver the nucleic acids into the analysis component, for example, PCR component of the instrumentation; conduct the analysis, such as PCR; and present the results, for example, display on a screen, provide a printout, save on a computer system, or transmit the results to a remote computer system. Thus, the cartridges disclosed herein could be used in the appropriate sample analytical instrumentation, such as Abbott's ID NOW™ instrumentation, where the only user mediated step is loading of the sample into the cartridge and loading the cartridge into the analytical instrument (not necessarily in that order). The appropriate computer program that controls the existing sample analytical instrument can be revised to operate and process the samples from a cartridge disclosed herein. In comparison to such an automated cartridge and sample analytical instrument, conventional sample processing devices and instrumentation require a user to manually perform bind-wash-elute processes using a solid phase support (e.g., silica membrane or silica beads).

FIG. 14 shows a typical sample processing workflow using a sample preparation system comprising a sample preparation cartridge and a magnet disclosed herein. The first chamber of the cartridge is filled with a sample, lysis buffer and PMPs. The PMPs are initially in solution. After sample lysis, released nucleic acids bind to the PMPs (see FIG. 14, steps 1-2). The PMPs are washed by exposing the PMPs to a magnetic force to form an aggregate and transporting the aggregated PMPs through the second chamber of the cartridge into the third chamber which comprises an elution buffer (see FIG. 14, step 3). For nucleic acid elution, magnetic force is removed and the PMPs are mixed with the elution buffer to release the nucleic acids from the PMPs (see FIG. 14, step 4).

Figure 15:
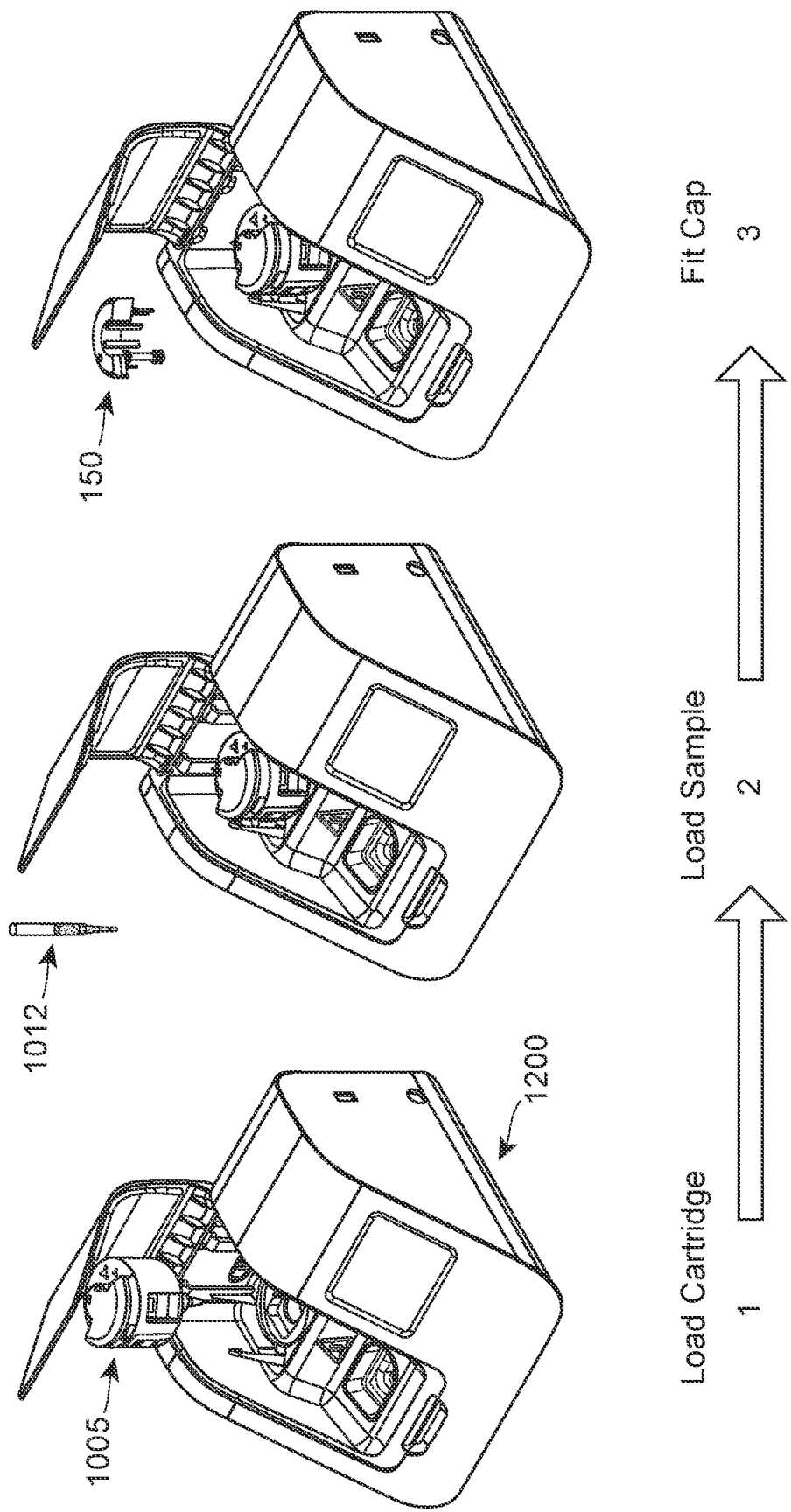
FIG. 15 shows a schematic representation of a sample preparation cartridge used in an analytical instrument, such as Abbott ID NOW™. In this example, the cartridge is installed in the analytical instrument, a sample is loaded into the cartridge, and, without further user mediated steps, the sample is analyzed to output the results.
Figure 16:
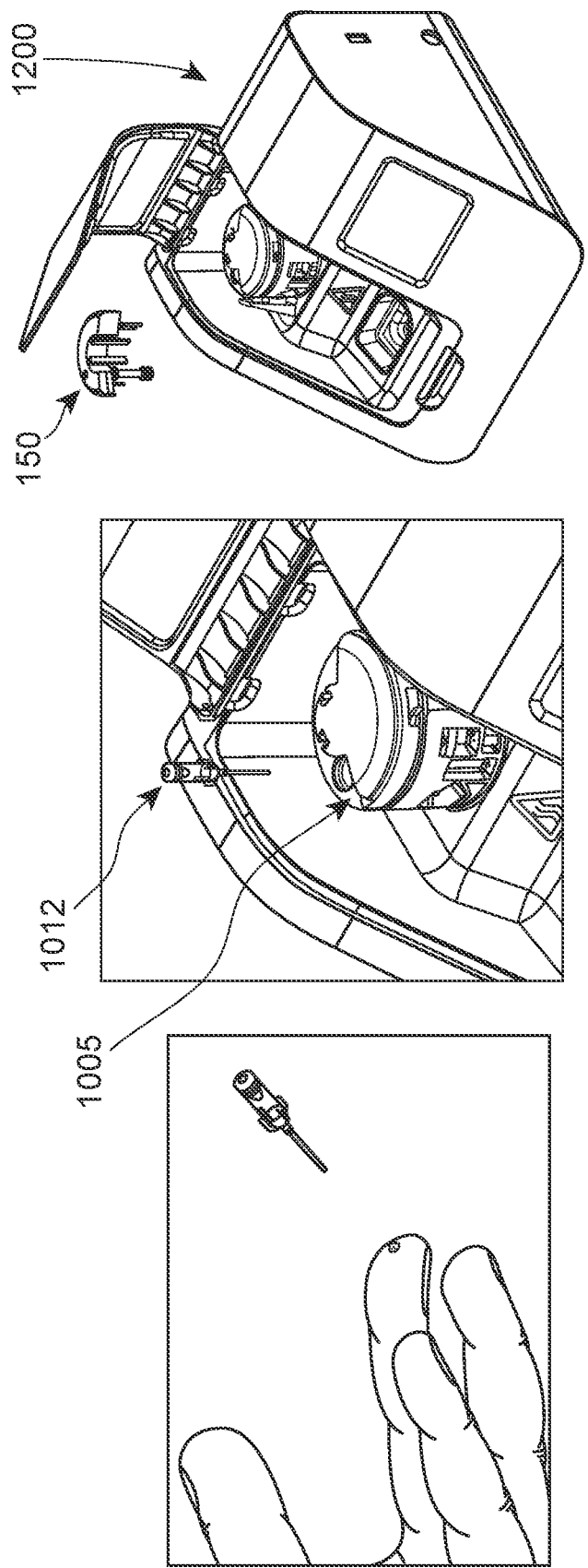
FIG. 16 shows a schematic representation of a sample preparation cartridge and analytical instrument used to analyze a subject's blood sample. The blood is collected and loaded into the cartridge installed in the analytical instrument, and, without further user mediated steps, the blood sample is analyzed to output the results.

An example of an automated cartridge and sample analytical instrument is provided in FIGS. 15 and 16. The cartridge is configured to work in conjunction with a current analytical instrument, such as Abbott ID NOW™ instrument. A sample preparation cartridge used in such automated analytical instrument is herein referred to as "integrated sample processing device" or ISPD. As exemplified in FIGS. 15 and 16, a sample 1012 can be prepared by loading the sample into a sample preparation cartridge 1005 loaded into a sample analytical instrument, placing the cartridge cap, closing the instrument, and starting the instrument. The only user involved steps are loading the cartridge into the sample analytical instrument and loading the sample into the cartridge (not necessarily in that order), placing the cartridge cap, closing the lid of the analytical instrument, and actuating the instrument to analyze the sample. FIG. 16 shows a point-of-care procedure for using the sample preparation system which involves placing a blood sample 1012 into the first chamber of the sample preparation cartridge 1005, placing the cap 150 over the cartridge and closing the lid of the instrument 1200.

FIG. 17 shows various components of an example of a sample preparation cartridge 110 (integrated sample processing device (ISPD)) and two types of cylinder housings 600 that can be used to isolate nucleic acids using paramagnetic particles.

Figure 18A:
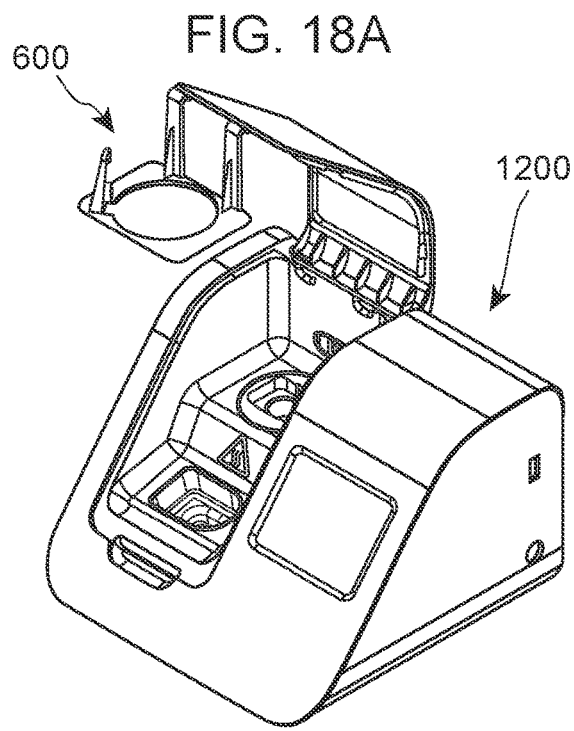
FIGS. 18A-18D show configuring an existing sample processing instrument, such as Abbott ID NOW™ instrument to include a cylinder housing. A removable cylinder housing allows flexibility for the use of sample processing device for other types of sample analysis, i.e., sample analysis that do not involve the use of the sample preparation cartridges disclosed herein.
Figure 18B:
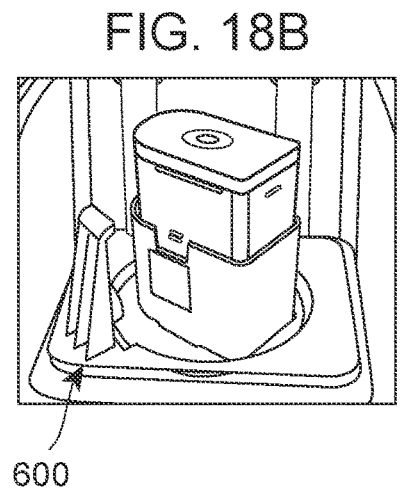
Figure 18C:
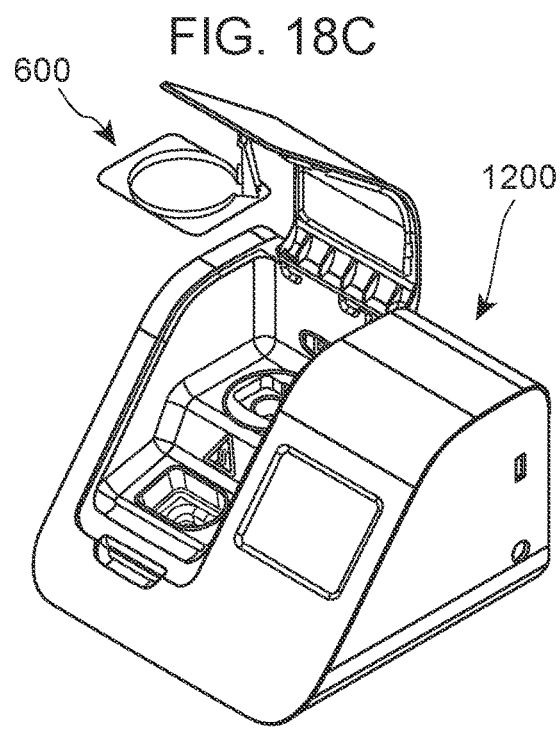
Figure 18D:
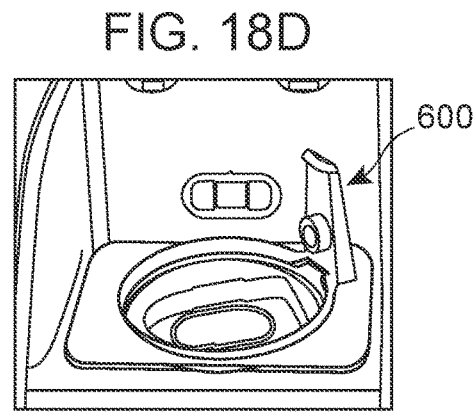

The magnet portion of the sample preparation system can be provided as a part of the instrument or as an accessory, for example, as a cylinder housing 600 shown in FIG. 17. The cylinder housing 600 can be configured to fit into a sample analytical instrument, such as Abbott ID NOW™. Certain such examples are provided in FIG. 17. The cylinder housing may include a means for attaching the housing to the instrument. Such means can include an adhesive. In certain instances, the means comprises snap-in feature(s). Such features include one or more grooves that receive a mating protrusion(s) disposed in the instrument or vice versa. An embodiment in which a cylinder housing with two supports extending up from the flat region of the cylinder housing and including in the top regions protrusions that snap into indentations in the instrument is shown in FIGS. 18A and 18B. In other instances, the bottom flat region of a cylinder housing may have a layer of adhesive covered with a peel-off tape. Such an embodiment is depicted in FIGS. 18C and 18D. As such, an ISPD device as exemplified in FIGS. 18A-18D provides robustness and reliability. Because of minimal user participation, the ISPD in combination with appropriate analytical instrument is suitable for automated sample analysis.

Methods

As summarized above, provided by the present disclosure are methods. In certain aspects, the methods are methods of preparing a nucleic acid sample. Such methods include mixing a sample comprising cells, virus, bacteria, fungi, etc., with a lysis buffer in a lysis chamber of sample preparation cartridge, comprising: a cylindrical structure, comprising: an annular wall, a plurality of cavities in the annular wall configured to form open-sided chambers on the annular wall, and one or more interconnections providing fluidic communication between chambers; one or more covers that cover the open side of the chambers. The lysis buffer or the chamber may have PMPs. Alternatively, the methods further include mixing paramagnetic particles (PMPs) into a mixture of the sample and lysis buffer, and agitating the mixture and allowing nucleic acids in the sample or released from the cells, virus, bacteria in the sample to bind to the paramagnetic particles. The methods further include rotating the cylindrical structure to a first position to allow a magnet to be positioned proximal to the cover and magnetically capture the paramagnetic particles in the lysis chamber; rotating the cylindrical structure to a second position to transfer the paramagnetic particles from the lysis chamber to an immiscible phase chamber comprising an immiscible phase (e.g., oil or air); and rotating the cylindrical structure to a third position to transfer the nucleic acids from the immiscible phase chamber to an elution chamber of the device comprising an elution buffer.

In certain aspects, the sample is a sample of whole blood, serum, plasma, sputum, nasal fluid, saliva, mucus, semen, vaginal fluid, a tissue, organ, and/or the like of a mammal (e.g., a human, a rodent (e.g., a mouse), or any other mammal of interest). In other aspects, the sample is a collection of cells from a source other than a mammal, such as bacteria, yeast, insects (e.g., *Drosophila*), amphibians (e.g., frogs (e.g., *Xenopus*)), viruses, plants, or any other non-mammalian nucleic acid sample source.

In certain aspects, rotating the sample preparation cartridge from a first position to a second position comprises rotating the sample preparation cartridge so that the entire span of the lysis chamber is rotated across the magnet. That is, the sample preparation cartridge may be rotated such that the entire lateral span of the lysis chamber is exposed to the magnet.

Similarly, in certain aspects, rotating the sample preparation cartridge from a second position to a third position comprises rotating the sample preparation cartridge so that the entire span of the immiscible phase chamber is rotated across the magnet. That is, the sample preparation cartridge may be rotated such that the entire lateral span of the immiscible phase chamber is exposed to the magnet.

The methods of the present disclosure may include the additional steps of filling the lysis chamber with a lysis buffer and paramagnetic particles from a fluid pack housed within a buffer pack and filling an elution chamber with an elution buffer from a fluid pack housed within the buffer pack. In embodiments utilizing a non-air immiscible phase, the steps may additionally include filling an immiscible phase chamber with an immiscible phase from a fluid pack housed within the buffer pack.

In certain embodiments, fluid is transferred from a fluid pack housed within a buffer pack to a chamber by applying pressure to the fluid in the fluid pack to force the fluid through channels in the cylindrical structure of the sample preparation device. For example, the fluid may comprise a lysis buffer, in some cases including paramagnetic particles, an immiscible phase and an elution buffer. In some cases, the immiscible phase comprises oil.

When fluid is transferred from a fluid pack, in certain embodiments, pressure is applied to the fluid in the fluid pack by applying mechanical force to a cap of the sample preparation device that comprises arms to engage the fluid pack. By cap, it is meant any convenient mechanical structure with arms to engage the fluid pack. For example, the cap may comprise a substantially flat base from which arms protrude from one side such that when force is applied to the flat side of the cap, such force is transferred along the arms protruding from the base, which in turn engage fluid in the fluid pack thereby applying pressure to the fluid in the fluid pack and forcing it through channels in the cylindrical structure.

The methods of the present disclosure may include the additional step of transferring eluted nucleic acids out of the elution chamber of the sample preparation device by plunging the contents of the elution chamber through a drain hole in the chamber. Plunging the elution chamber may take any convenient form. For example, the sample preparation device may include a plunger assembly, including a plunger configured to engage the elution chamber that may be automatically triggered to plunge the elution chamber upon rotating the cylindrical structure to a specified position.

When the eluted nucleic acids are plunged out of the elution chamber, in certain embodiments, the sample preparation device further comprises a plunger, a spring and a trigger interlocked together so that plunging the elution chamber comprises applying pressure to the trigger to release tension on the spring thereby driving the plunger into the elution chamber. In certain embodiments, the cylindrical structure is rotated to a fourth position to allow a mechanical arm to apply pressure to the trigger. In such cases, the trigger may protrude beyond the exterior radius of the cylindrical structure. By mechanical arm, it is meant any convenient device for use in depressing the trigger. For example, such a mechanical arm may be mounted in a fixed location and positioned to engage the trigger only when the cylindrical device is rotated to a position where the mechanical arm abuts the trigger.

In certain embodiments, a sample comprising cells is introduced to the lysis buffer by applying pressure to a sample input component of the sample preparation device and thereby introducing the sample comprising cells to the lysis buffer. By sample input component, it is meant any convenient structure for enclosing cells such that when a force is applied to the enclosure, pressure is applied to the sample thereby forcing the sample into the lysis chamber of the sample preparation device.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A sample preparation cartridge, comprising:
   a cylindrical structure, comprising:
   a top end,
   a bottom end,
   an annular wall extending between the top and bottom ends,
   a plurality of chambers located on the annular wall, wherein the chambers extend between an exterior surface of the annular wall and an interior of the cylindrical structure,
   wherein the annular wall comprises cavities forming an open side of each of the chambers; and
   one or more channels providing fluidic communication between the plurality of chambers, wherein the channels are formed by recesses in the annular wall and comprise an open side; and
   one or more covers affixed over exterior surface of the annular wall to cover and fluidically seal the open side of the chambers and the open side of the channels.

2. The sample preparation cartridge according to claim 1, wherein the plurality of chambers comprises at least three chambers.

3. The sample preparation cartridge according to claim 1, wherein the recesses extends between lateral sides of two adjacent chambers.

4. The sample preparation cartridge according to claim 1, wherein the recesses are positioned on lateral sides of one or more chambers at a substantially constant height above the bottom end of the cylindrical structure.

5. The sample preparation cartridge according to claim 1, wherein the shape of a chamber is such that a lateral portion of the chamber that is proximal to channels tapers towards the channel.

6. The sample preparation cartridge according to claim 1, wherein one or more of the chambers comprises an opening, wherein the opening is configured for venting of the chamber, filling of the chamber with a fluid, and/or draining of fluid from the chamber.

7. The sample preparation cartridge according to claim 1, wherein the plurality of chambers comprises a first chamber, a second chamber and a third chamber, wherein the second chamber is positioned between the first and third chambers.

8. The sample preparation cartridge according to claim 7, wherein the first chamber comprises an opening at the top of the chamber, wherein the opening is configured as an inlet.

9. The sample preparation cartridge according to claim 8, wherein the inlet is configured as an inlet for introducing a lysis buffer, a sample, and/or a mixture thereof.

10. The sample preparation cartridge according to claim 7, wherein the first chamber comprises a compartment positioned on the bottom region or underneath the bottom region of the first chamber, wherein the compartment comprises an opening fluidically connecting the compartment to the interior of the first chamber, wherein the compartment comprises paramagnetic particles (PMPs) disposed therein, optionally wherein the PMPs are lyophilized.

11. The sample preparation cartridge according to claim 10, where the first chamber comprises an opening at the bottom of the chamber, wherein the opening is configured as an inlet for lysis buffer and wherein the first chamber comprises an opening at the top of the first chamber configured as a sample inlet.

12. The sample preparation cartridge according to claim 10, wherein the compartment comprises an inlet fluidically connecting the compartment to a channel and an outlet fluidically connecting the compartment to the interior of the first chamber.

13. The sample preparation cartridge according to claim 7, wherein the second chamber does not include an opening other than the interconnections with the first and third chambers.

14. The sample preparation cartridge according to claim 13, wherein the third chamber comprises an opening at a bottom region of the chamber, wherein the opening is configured for draining the third chamber.

15. The sample preparation cartridge according to claim 14, wherein the opening at the bottom of the third chamber is fluidically connected to one or more collection containers.

16. The sample preparation cartridge according to claim 14, wherein the third chamber comprises an opening at a bottom region of the chamber wherein the opening is distinct from the opening for draining the third chamber and is configured for filling the third chamber.

17. The sample preparation cartridge according to claim 7, wherein the first chamber is fluidically connected to a well comprising lysis buffer.

18. The sample preparation cartridge according to claim 7, wherein the first chamber comprises a lysis buffer.

19. The sample preparation cartridge according to claim 7, wherein the second chamber comprises an immiscible phase.

20. The sample preparation cartridge according to claim 19, wherein the immiscible phase comprises oil.

21. The sample preparation cartridge according to claim 19, wherein the immiscible phase comprises air.

22. The sample preparation cartridge according to claim 1, wherein the interior of the cylindrical structure comprises one or more wells.

23. The sample preparation cartridge according to claim 22, further comprising channels in the cylindrical structure that provide fluidic communication between the wells and one or more of the plurality of chambers.

24. The sample preparation cartridge according to claim 23, wherein each well is interconnected with a distinct chamber via one or more channels.

25. The sample preparation cartridge according to claim 1, further comprising a buffer pack.

26. The sample preparation cartridge according to claim 25, wherein the buffer pack comprises one or more fluid packs.

27. The sample preparation cartridge according to claim 26, wherein the fluid packs comprise each of a lysis buffer pack and an elution buffer pack.

28. The sample preparation cartridge according to claim 27, wherein the fluid packs further comprise an immiscible phase pack.

29. The sample preparation cartridge according to claim 28, wherein the immiscible phase comprises an oil.

30. The sample preparation cartridge according to claim 28, wherein the immiscible phase comprises air.

31. The sample preparation cartridge according to claim 27, wherein the lysis buffer pack further comprises paramagnetic particles.

32. The sample preparation cartridge according to claim 25, wherein the buffer pack fits within the wells.

33. The sample preparation cartridge according to claim 27, wherein the lysis buffer pack is placed in a well fluidically connected to the first chamber.

34. The sample preparation cartridge according to claim 27, wherein the elution buffer pack is placed in a well fluidically connected to the third chamber.

35. The sample preparation cartridge according to claim 28, wherein the immiscible phase pack is placed in a well fluidically connected to the second chamber.

36. The sample preparation cartridge according to claim 1, further comprising a sealing lid assembly comprising:
   a sealing plate positioned on the top end of the cylindrical structure; and
   a protective cover positioned on the top of the sealing plate, wherein the protective cover encloses the sealing plate.

37. The sample preparation cartridge according to claim 36, further comprising a cap configured for positioning on the top of the cover.

38. The sample preparation cartridge according to claim 37, wherein the cap comprises one or more arms positioned to mechanically engage the buffer pack disposed in the one or more wells in the cylindrical structure.

39. The sample preparation cartridge according to claim 38, wherein the sealing plate further comprises a plunger assembly comprising:
   a plunger comprising a gasket seal mounted on a shaft;
   a spring; and
   a trigger that engages the spring and the shaft.

40. The sample preparation cartridge according to claim 39, wherein the spring applies tension to the plunger in a retracted position.

41. The sample preparation cartridge according to claim 40, wherein the trigger and the spring are mechanically interlocked so that the trigger is armed when the plunger is in the retracted position.

42. The sample preparation cartridge according to claim 41, wherein the gasket seal of the plunger is positioned to engage with one of the chambers.

43. The sample preparation cartridge according to claim 42, wherein the trigger protrudes from the cylindrical structure.

44. The sample preparation cartridge according to claim 43, wherein the trigger is oriented to be depressed in a lateral direction.

* * * * *